US008744816B1

(12) United States Patent
Bosch

(10) Patent No.: US 8,744,816 B1
(45) Date of Patent: Jun. 3, 2014

(54) EVALUATION OF DATABASE RECORDS

(76) Inventor: Ryan G. Bosch, McLean, VA (US)

( * ) Notice: Subject to any disclaimer, the term of this patent is extended or adjusted under 35 U.S.C. 154(b) by 868 days.

(21) Appl. No.: 12/714,092

(22) Filed: Feb. 26, 2010

Related U.S. Application Data

(63) Continuation of application No. 09/435,358, filed on Nov. 8, 1999, now abandoned.

(51) Int. Cl.
*G06Q 10/00* (2012.01)
*G06Q 50/10* (2012.01)

(52) U.S. Cl.
USPC .................................. 703/3; 703/2

(58) Field of Classification Search
USPC ......................................... 705/2, 3
See application file for complete search history.

(56) References Cited

U.S. PATENT DOCUMENTS

| | | | |
|---|---|---|---|
| 5,084,819 A | 1/1992 | Dewey et al. | |
| 5,301,105 A | 4/1994 | Cummings, Jr. | |
| 5,619,991 A | 4/1997 | Sloane | |
| 5,660,176 A | 8/1997 | Iliff | |
| 5,711,297 A | 1/1998 | Iliff | |
| 5,724,968 A | 3/1998 | Iliff | |
| 5,754,111 A | 5/1998 | Garcia | |
| 5,764,923 A | 6/1998 | Talmann et al. | |
| 5,832,488 A | 11/1998 | Eberhardt | |
| 5,868,669 A | 2/1999 | Iliff | |
| 5,879,163 A | 3/1999 | Brown et al. | |
| 5,897,620 A | 4/1999 | Walker et al. | |
| 5,908,383 A | 6/1999 | Brynjestad | |
| 5,910,107 A | 6/1999 | Iliff | |
| 5,911,132 A | 6/1999 | Sloane | |
| 5,911,687 A | 6/1999 | Sato et al. | |
| 5,913,197 A | 6/1999 | Kameda | |
| 5,915,240 A | 6/1999 | Karpf | |
| 6,032,119 A * | 2/2000 | Brown et al. | 705/2 |
| 6,049,794 A | 4/2000 | Jacobs et al. | |
| 6,129,744 A * | 10/2000 | Boute | 607/25 |
| 6,139,494 A * | 10/2000 | Cairnes | 600/300 |
| 6,247,004 B1 | 6/2001 | Moukheibir | |

(Continued)

OTHER PUBLICATIONS wysiwyg://46/https://alllhealth.wellmed.com/hw/Questions1.asp, Dec. 12, 1999, pp. 1-3.

(Continued)

*Primary Examiner* — Robert Morgan
*Assistant Examiner* — Charles P. Coleman
(74) *Attorney, Agent, or Firm* — Harrity & Harrity, LLP

(57) ABSTRACT

A system includes a database and one or more computer devices. The database is configured to store database records associated with a group of users. The one or more computer devices is/are configured to receive data from a user; store the data in a database record in the database, where the database record is associated with the user; automatically evaluate the data, in the database record, to generate a set of first recommendations, where each of the first recommendations relates to a recommended action to be taken by the user; select individuals based on the data in the database record; transmit the data, from the database record, to each of the individuals; receive a second recommendation from each of at least two of the individuals, where each of the second recommendations relates to another recommended action to be taken by the user; compile the second recommendations, from the at least two individuals, to generate a set of second recommendations, where the set of second recommendations is different from the set of first recommendations, and provide the set of first recommendations and the set of second recommendations to the user.

24 Claims, 35 Drawing Sheets

(56) References Cited

U.S. PATENT DOCUMENTS

| | | | |
|---|---|---|---|
| 6,270,456 B1 | 8/2001 | Iliff | |
| 2008/0177578 A1* | 7/2008 | Zakim | 705/3 |
| 2008/0243547 A1* | 10/2008 | Brett et al. | 705/3 |
| 2009/0276242 A1* | 11/2009 | Waisbren | 705/2 |

OTHER PUBLICATIONS wysiwyg://45/https://allhealth.wellmed.com/hg/Intro.asp, Dec. 12, 1999, pp. 1-2.
http://www.drkoop.com/wellness/prevention, Dec. 5, 1999, p. 1.
http://www.drkoop.com/advice.asp?sessionid=9093, Jul. 29 1999, pp. 1-18.
Integrated Healthcare Report, Healthcare @ The Speed of Thought, May 1999, pp. 1-20.
http://www.allhealth.com, Jan. 7, 2000, pp. 1-3.
www.healthwindows.com/HealthWindows/newindex.asp, Sep. 14, 1999, p. 1.
www.healthwindows.com/HealthWindows/what_we_offer.asp, Sep. 14, 1999, pp. 1-2.
https://healthapp.healtheon.com/hshra/hraopen.html, Jun. 1, 1999, p. 1.
www.drkoop.com/prevcenter/care, Jul. 29, 1999, pp. 1-2.
www.drkoop.com/prevcenter/care/adult.asp, Jul. 29, 1999, pp. 1-2.
www.drkoop.com/prevcenter/care/adult-cancer.asp, Jul. 29, 1999, pp. 1-2.
www.drkoop.com/prevcenter/care/adult-immuz.asp, Jul. 29, 1999, p. 1.
www.drkoop.com/prevention/a...?sessionid=9093&justdoctoradvice=1, Jul. 29, 1999, pp. 1-5.
wysiwyg://102/http://go.drkoop.com/prevcenter/care/adult-tests.asp, May 28, 1999, pp. 1-2.
wysiwyg://106/http://go.drkoop.com/prevcenter/care/men.asp, May 28, 1999, pp. 1-2.
wysiwyg://15/http://www.forbes.com/forbes/99/0517/6310178a.htm, Jun. 4, 1999, pp. 1-9.
www.rxdata.net/about.htm, May 28, 1999, pp. 1-2.
www.rxdata.net/addons.asp, May 28, 1999, pp. 1-2.
www.rxdata.net/immunizations.asp, May 28, 1999, pp. 1-2.
www.rxdata.net/PeopleHome.asp, Jul. 25, 1999, p. 1.
www.rxdata.net/hardcopy.asp, Jul. 25, 1999, p. 1-2.

* cited by examiner

GENDER: Male ○ Female ●

Fig. 3A

■ Tonsils ☐ Appendix ■ Hernias ☐ Other

Fig. 3B

NAME: Jane C. Public

Fig. 3C

EVALUATION OF DATABASE RECORDS

RELATED APPLICATION

This application is a continuation of U.S. patent application Ser. No. 09/435,358, filed Nov. 8, 1999, which is incorporated herein by reference.

BACKGROUND

As health care costs continue to rise, physicians are increasingly forced to search for new ways to provide efficient, effective medical services to their patients. It is known in the medical arts that a systematically administered preventative health care program reduces the occurrence of disease and controls the severity of disease, ultimately increasing the length and quality of a patient's life. However, existing preventative health care programs increase time and money spent on health care by requiring multiple office visits by patients, significant physician and patient time involvement, expensive and often redundant services, and frequent patient travel between hospitals, laboratory centers, and physician's offices.

SUMMARY

The present invention reduces or eliminates these inefficiencies while enhancing the effectiveness of medical services by utilizing communication and computer technology to automate certain aspects of preventative health care, reducing travel and time required for visits to health care providers by allowing patients to quickly and securely send and receive personal health information. The present invention is an integrated preventative medical services network that allows physicians to automate acquisition of patient medical information, review of patient medical records, retrieval of emergency medical records, formulation of preventative medicine and STANDARD OF CARE recommendations, coordination and tracking of recommendation implementation, and physician-patient communication involved in providing these services.

Registered service members use e-mail, a form posted on the Internet, a facsimile, or postal mail to provide personal medical information that is recorded in a database record called a MEDCHART. A member's MEDCHART is retained in secure electronic medical record storage and is accessible only to the member and to network-designated physicians. The network periodically performs an automated evaluation, called a HEALTHSCREEN, of each member's MEDCHART information and generates member-specific preventative medicine recommendations. In addition, network-designated physicians periodically evaluate each member's MEDCHART, formulating an expert STANDARD OF CARE (SOC) medical review for each member. The SOC is composed of specific recommendations for ongoing care of a member's existing medical conditions. The SOC and HEALTHSCREEN are key lists of network medical recommendations.

The network's DOCCONNECTOR service communicates a member's HEALTHSCREEN and the SOC review to the member, the member's personal physician, and Screening Procedure Centers (SPC's). The DOCCONNECTOR's dedicated server hosts an e-mail system and wide area network that coordinates implementation of these medical recommendations by the SPC's for each member, then reports results back to the member's personal physician. The member's personal physician may not be affiliated with the network. The member's personal physician interprets test results and reports back to the member via the DOCCONNECTOR service. The DOCCONNECTOR service incorporates these results into the member's existing MEDCHART record.

A member with questions may use the DIRECTDOC communication service to engage in direct correspondence with network physicians regarding specific health care issues. An emergency health care provider may, in an emergency, access a member's EMERGENCY MEDCHART, which is a network database record separate from the member's MEDCHART. The EMERGENCY MEDCHART contains MEDCHART medical information pre-selected by the member, and may contain some or all MEDCHART data at the member's discretion. Both member medical information and procedures for accessing an EMERGENCY MEDCHART may be printed or encoded on emergency WALLETCARDs, which are wallet-sized portable media issued to members. The information and passwords on WALLETCARDs can also be encoded on bracelets or stored on computer discs.

Within this integrated preventative medical services network, an authorized adult registered member can access the system on behalf of a registered child or infant. The preferred mode of communication between the member and the network is e-mail, which is encrypted for further confidentiality. The system may additionally or alternatively use other means of communication such as facsimile transmissions, voice mail, or the postal system.

Implementations consistent with the principles of the invention are illustrated below in the drawings and in the detailed description that follows.

BRIEF DESCRIPTION OF THE DRAWINGS

FIG. 3A shows a pair of radio buttons with which an applicant has disclosed female gender by pointing a computer screen cursor at an appropriate radio button and depressing a mouse button.

FIG. 3B shows a set of check boxes, all of which may be simultaneously selected as appropriate.

FIG. 3C shows a text field in which an applicant has typed her name.

DETAILED DESCRIPTION

An Integrated Preventative Medical Services network (hereinafter referred to as an "IPMS network") may be operated and maintained by a physician, a private medical group, a hospital, a health maintenance organization, a government-sponsored health organization, an insurance provider, or any other entity or combination of entities involved in the delivery of health care. The components of the network may reside at a single geographic location or be dispersed among any number of interconnected but geographically separate sites. Health care providers may assume responsibility for most or all aspects of system operation, or may delegate many system operations and maintenance functions to independent contractors such as Internet Service Providers (ISP's) or information systems specialists. Network affiliated physicians and screening procedure centers (SPC) will be involved in the functions of the IPMS network.

Figure 1:
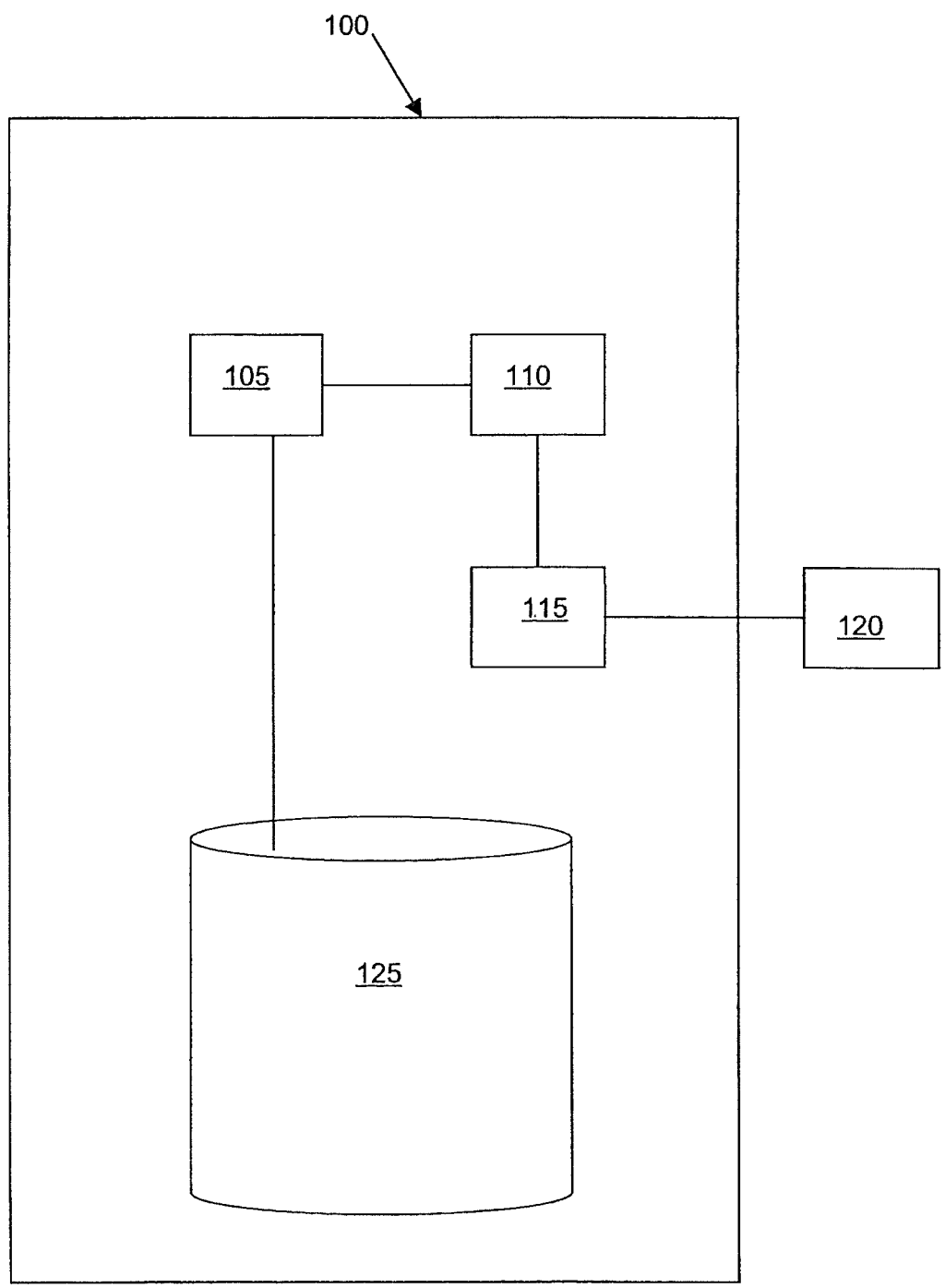
FIG. 1 shows a network server site.

In a preferred embodiment, an IPMS network has one or more network servers hosting one or more internet web sites through which network users access and input network data. FIG. 1 shows a network server site 100. Each web site can be hosted on a MICRON PENTIUM III 500 megahertz web server 105 with 128 megabytes of RAM. Each server can be connected to internet services 120 through CISCO SYSTEMS CATALYST 5500 switches 110, a Domain Name Server (DNS) 112, and CISCO SYSTEMS 7500 routers 115 utilizing the BGP4 data protocol. Routers are redundantly connected to internet services 120 such as those provided by UUNET, MCI, SPRINT, and PACIFIC BELL. Data are stored on at least one mass storage device 125 as is known in the art. The web servers can run MICROSOFT INTERNET INFORMATION SERVER 4.0 software under the MICROSOFT WINDOWS NT 4.0 operating system. E-mail can be processed by PENTIUM III E-mail servers 107 as are known in the art. E-mail servers can connect with web server 105 and CISCO SYSTEMS CATALYST 5500 switches 110.

Figure 2:
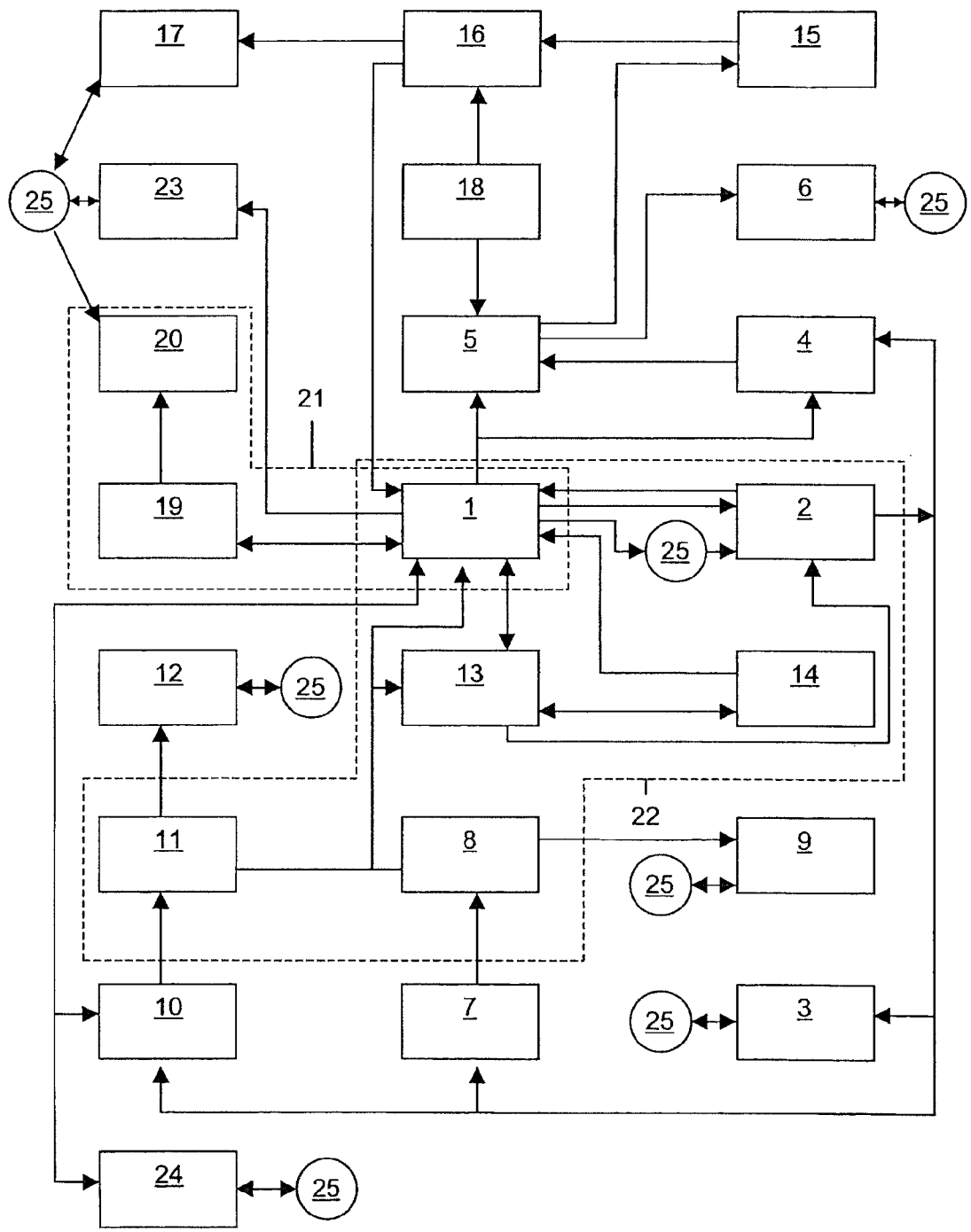
FIG. 2 is a flow diagram of Integrated Preventative Medical Service (IPMS) network functions.

FIG. 2 is a flow diagram of a preferred embodiment of IPMS network functions. A member 1 provides data to create a MEDCHART 2, which is encrypted and stored in a MICROSOFT ACCESS 97 database file 3 residing on one or more servers. Database file 3 may be accessed by network administrative staff 25 for specified administrative purposes. The MEDCHART 2 may be viewed and modified at any time by a member 1. The MEDCHART 2 can be processed by several MICROSOFT VISUAL BASIC 6.0 database scripts to produce different information products. A copy of the MEDCHART 2 is processed by a HEALTHSCREEN script 7 to produce the HEALTHSCREEN 8, which is stored in a database file 9. Database file 9 may be accessed by network administrative staff 25 for specified administrative purposes. The HEALTHSCREEN 8 is also transmitted both to the member 1 and at the member's discretion to the member's Personal Physician 13.

An EMERGENCY MEDCHART script 4 may be activated by the member 1 to process another copy of the MEDCHART 2, producing an EMERGENCY MEDCHART 5, which is encrypted and stored in a database file 6. Database file 6 may be accessed by network administrative staff 25 for specified administrative purposes. The member 1 may at any time access the EMERGENCY MEDCHART 5 to modify its contents. The EMERGENCY MEDCHART 5 may also be accessed by an Emergency Health Care Provider 18. A copy of the EMERGENCY MEDCHART 2 may be processed by a WALLETCARD script 15 to produce a WALLETCARD 16, which is both stored electronically in a database file 17 and provided to the member 1. Database file 17 may be accessed by network administrative staff 25 for specified administrative purposes. An Emergency Health Care Provider 18 may use information provided on the WALLETCARD 16 to access an EMERGENCY MEDCHART 5.

Additional copies of the MEDCHART 2 are sent to Network-Affiliated Subspecialty Physicians 10, who create a STANDARD OF CARE Review 11. The STANDARD OF CARE Review 11 is sent to the member 1 and at the member's discretion to the member's Personal Physician 13, and stored in a database file 12. Database file 12 may be accessed by network administrative staff 25 for specified administrative purposes. Network-Affiliated Subspecialty Physicians 10 may interact with the member 1 to obtain information pertaining to member health status. Communications between a member 1 and Network-Affiliated Subspecialty Physicians 10 are stored in a database file 24. Database file 24 may be accessed by network administrative staff 25 for specified administrative purposes.

The DIRECTDOC 21 communication service allows a member 1 to interact with a designated Network Physician 19 to obtain health care information. All DIRECTDOC 21 communications are stored in a database file 20. Database file 20 may be accessed by network administrative staff 25 for specified administrative purposes. Any facsimile or postal mail communications from a member 1 are converted to a suitable digital form and stored in a database file 23. Database file 23 may be accessed by network administrative staff 25 for specified administrative purposes.

A non-network Personal Physician 13 may interact with a Screening Procedure Center 14 to order tests and to obtain test results. The Screening Procedure Center 14 may contact a member 1 to coordinate tests ordered. The DOCCONNECTOR communication service 22 provides fast, secure communication between a member 1, a Personal Physician 13, and a Screening Procedure Center 14, and provides secure access to a member's MEDCHART 2, HEALTHSCREEN 8, and SOC Review 11.

A prospective member subscribes to an IPMS network by providing personal information and his or her medical history for evaluation. In a preferred embodiment, the member may complete an Internet web page questionnaire by accessing an IPMS network Internet web site and providing appropriate responses while online. The registration questionnaire is created with Hypertext Markup Language (HTML), as is known in the art. Responses may be provided by marking check boxes or radio buttons and by typing text into text fields, all as are known in the art. Radio buttons are sets of check boxes in which a user-placed mark in any box in the set automatically removes any mark in any other box in the set, so that only one box in the set may be selected at a time. FIG. 3A shows a pair of radio buttons with which a member has disclosed female gender by pointing a computer screen cursor at an appropriate radio button and depressing a mouse button. FIG. 3B shows a set of check boxes, all of which may be simultaneously selected as appropriate. FIG. 3C shows a text field in which a member has typed her name.

The member's responses are collected from the web page questionnaire and inserted into appropriate record fields in a MICROSOFT ACCESS 97 database, for example, with scripts written in MICROSOFT VISUAL BASIC 6 or the like, as are known in the art. Alternatively, the member may request, download, complete, and return an e-mail version of the questionnaire. The e-mail questionnaire can be processed with MICROSOFT VISUAL BASIC 6.0 scripts that insert responses into appropriate record fields in the IPMS network's MICROSOFT ACCESS 97 database, or the like.

In still another embodiment, the member may complete the registration questionnaire on paper, then fax, mail, or in some other way send the completed questionnaire to the network. A member may also telephone an IPMS network and provide verbal disclosure of personal medical information to an IPMS network administrative staff member who asks each question on the registration questionnaire and records the member's responses. As shown in FIG. 2, after a member 1 has provided personal medical information in print, or as a member provides personal medical information verbally, the IPMS network administrative staff member 25 creates a MEDCHART 2 for the member 1 by entering questionnaire information into appropriate fields of the online registration questionnaire.

The database record thus created is called a member's MEDCHART. The MEDCHART is an individual, permanent, and secure database record containing a member's personal medical information, stored in any format that both the lay public and a physician can comprehend and utilize. In a preferred embodiment, a MEDCHART contains the following categories: Past Medical History, Past Surgical History, Allergies, Medications, Social History, Family History, Physical Examination, and Medical Data. Medical Data information includes labwork, X-rays, Computerized Axial Tomography (CAT) scans (including Electron Beam CAT scans), Magnetic Resonance Imaging (MRI) scans, echoes, cardiac catheterizations, nuclear cardiac perfusion scans such as thallium scans, Technetium Sestamibi Scan (Cardiolyte Scan), ultrasounds, chromosome analysis, and genetic testing. The MEDCHART may contain additional categories as deemed desirable by the network.

The MEDCHART is securely stored, strictly password protected, and encrypted on all network transmissions using programs and methods well known in the art. A program may be any computer code sequence, and as such any program may operate independently, may contain other programs as components, may itself be a component of another program, and/or may interoperate with any number of other programs in any manner known in the art. Unless otherwise specified by the member, a member's MEDCHART can be accessed and modified only by the member. The subspecialty physicians designated by the IPMS network (network affiliated physicians) to perform the SOC review will be provided with a specific member's MEDCHART for the sole purposes of completing the SOC review. At the member's discretion, other designated people, such as the member's non-network personal physician or family members, can view but not modify the member's MEDCHART. Of course, other security and privacy measures are available to accommodate special needs of patients, such as providing access for legal guardians or parents of minors.

Once a member's MEDCHART record is created, the medical network performs a HEALTHSCREEN at a regular interval such as twice a year. The HEALTHSCREEN is a review of each member's MEDCHART record performed by a computer program that evaluates the member's MEDCHART data and generates a list of current Preventative Medicine recommendations with supporting references, tailored specifically to the member's individual medical risk factors. As an example, the computer program reviews a member's MEDCHART and identifies specific risk factors for prostate cancer, such as age, race, family history of prostate cancer, and other risks to be identified in the future, and determines the ideal member-specific recommendation for the timing and frequency of Prostate Specific Antigen (PSA) blood testing to screen for prostate cancer. The computer program then reviews the network member's MEDCHART to determine whether the member has had PSA testing within the literature-recommended time interval. If not, a recommendation for prostate cancer screening is included in the list of preventative medicine recommendations generated by the HEALTHSCREEN and communicated to the member.

In a preferred embodiment, the HEALTHSCREEN computer program generates preventative medical recommendations for risk reduction for the following conditions: prostate cancer, breast cancer, colon cancer, testicular cancer, skin cancer, cervical cancer, gastric cancer, coronary artery disease, cerebral vascular accidents, thyroid disease, glaucoma, vision loss, hearing loss, osteoporosis, diabetes, high blood pressure, iron deficiency, and vitamin deficiencies. The program may also generate recommendations for genetic conditions, other cancers, rare diseases, and other diseases. The complete HEALTHSCREEN is a compilation of disease-specific recommendations generated by the computer program and provided through the network to each member. If the member so desires, the HEALTHSCREEN can also be provided by the network's DOCCONNECTOR service to the member's personal physician.

Figure 4:
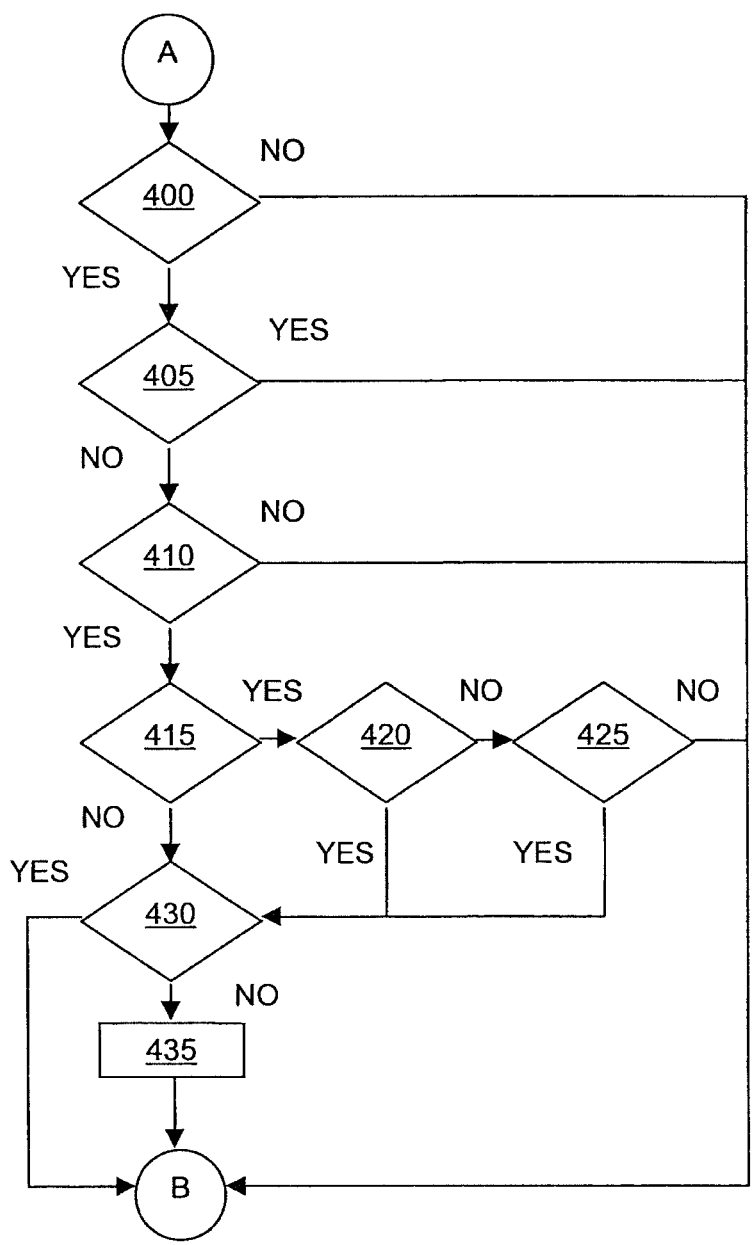
FIG. 4 depicts an algorithm for prostate cancer screening using rectal examinations.

A preferred embodiment of the HEALTHSCREEN algorithm processes each MEDCHART record with a sequence of algorithms. Each algorithm asks questions to determine whether the member meets certain MEDCHART criteria. For example, when no criteria relevant to an algorithm are satisfied, the algorithm generates no specific recommendation. FIG. 4 depicts an algorithm for prostate cancer screening using rectal examinations. If the member is male 400, has no personal history of prostate cancer 405 in his MEDCHART, is more than forty years old 410, is at least forty but less than fifty years old 415, is African-American 420 OR has a family history of prostate cancer 425, and has had no rectal exam in the past year 430, then HEALTHSCREEN will output a recommendation similar to the following recommendation 435: "Our records indicate that you are due for a screening rectal exam this year. More information on this Preventative Medicine topic may be found at http://www.edoc4u.com/prostate.html." If the member is male 400, has no personal history of prostate cancer 405 in his MEDCHART, is at least fifty years old 410, 415, and has had no rectal exam in the past year 430, then HEALTHSCREEN will output a recommendation similar to the following recommendation 435: "Our records indicate that you are due for a screening rectal exam this year. More information on this Preventative Medicine topic may be found at http://www.edoc4u.com/prostate.html." Members not meeting the network-determined criteria receive no recommendations from this algorithm. For example, female members would receive no recommendation from this algorithm. HEALTHSCREEN processing then continues.

Figure 5:
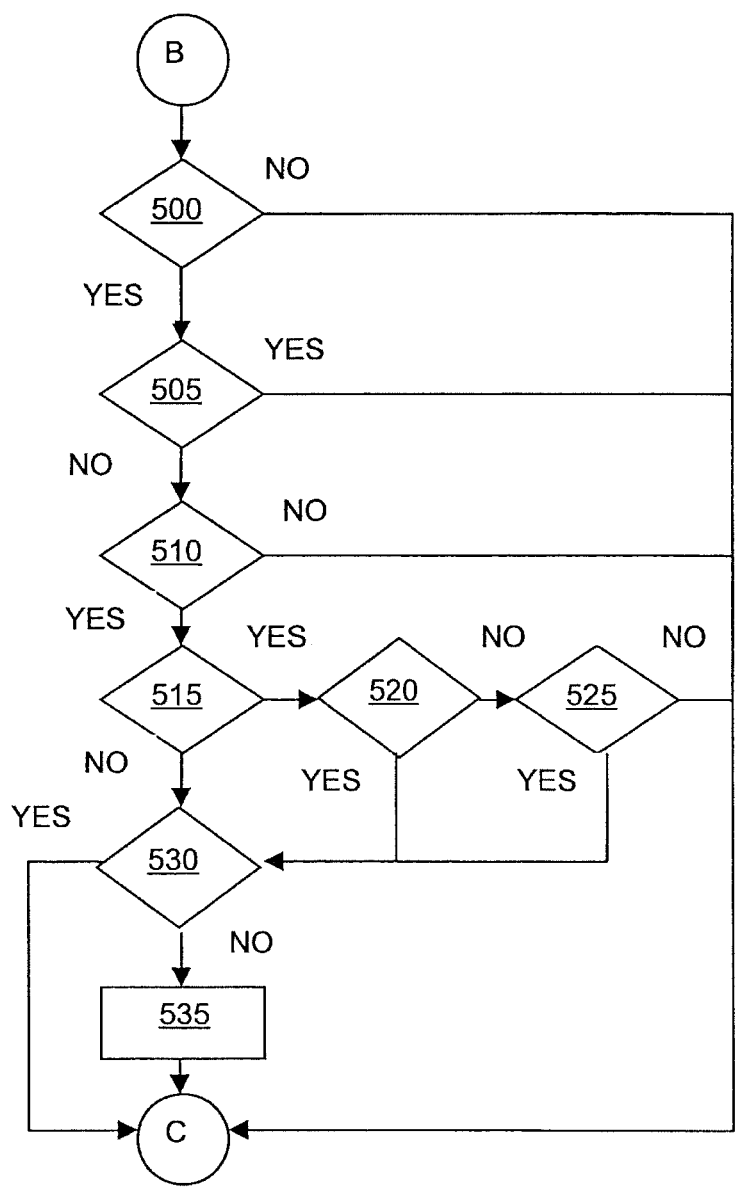
FIG. 5 depicts an algorithm for prostate cancer screening using Prostate Specific Antigen (PSA).

FIG. 5 depicts an illustrative algorithm for prostate cancer screening using Prostate Specific Antigen (PSA) testing. If the member is male 500, has no personal history of prostate cancer 505 in his MEDCHART, is more than forty years old 510, is at least forty but less than fifty years old 515, is African-American 5200R has a family history of prostate cancer 525, and has had no PSA test in the past year 530, then the HEALTHSCREEN will output a recommendation similar to the following recommendation 535: "Our records indicate that you are due for a screening PSA blood test this calendar year. More information on this Preventative Medicine topic may be found at http://www.edoc4u.com/psa.html." If the member is male 500, has no personal history of prostate cancer 505 in his MEDCHART, is more than forty years old 510, is at least forty and not less than fifty years old 515, and has had no PSA test in the past year 530, then HEALTHSCREEN will output a recommendation similar to the following recommendation 535: "Our records indicate that you are due for a screening PSA blood test this calendar year. More information on this Preventative Medicine topic may be found at http://www.edoc4u.com/prostate.html." Members not meeting the network-determined criteria receive no recommendations from this algorithm, and the HEALTHSCREEN processing continues.

Figure 6:
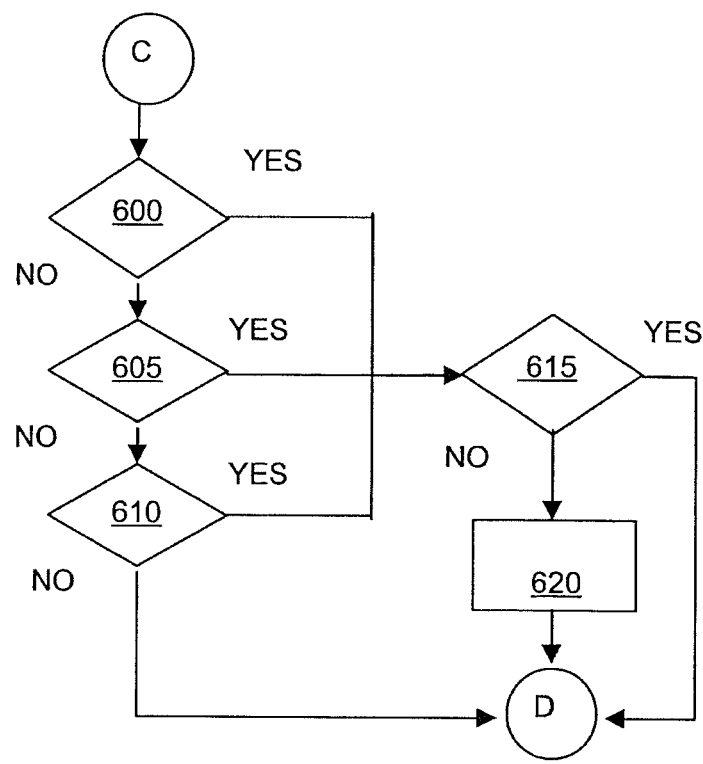
FIG. 6 depicts an algorithm for skin cancer screening using total body skin examination.

FIG. 6 depicts an illustrative algorithm for skin cancer screening using total body skin examination. If the member has a personal history of skin cancer 600 or a family history of melanoma 605 or is older than forty-four 610, and has had no total body skin exam in the past year 615, then HEALTHSCREEN will output a recommendation similar to the following recommendation 620: "Our records indicate that you are due for a total body skin examination this calendar year. More information on this Preventative Medicine topic may be found at http://www.edoc4u.com/skincan.html." Members not meeting the network-determined criteria receive no recommendation from this algorithm, and the HEALTHSCREEN processing continues.

Figure 7:
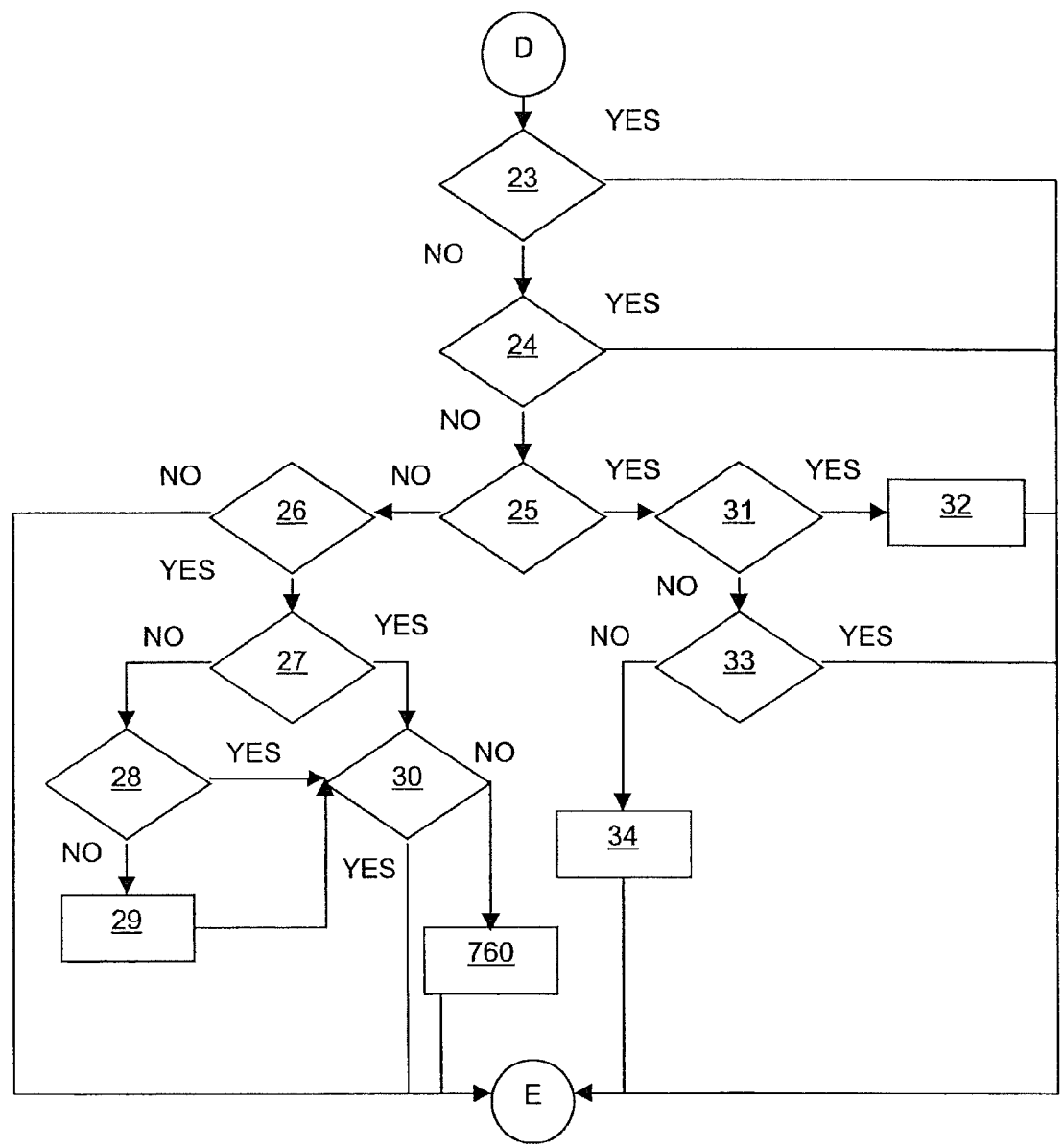
FIG. 7 depicts an algorithm for colon cancer screening with FOBT (Fecal Occult Blood Testing), FLEX SIG (Flexible Sigmoidoscopy), and colonoscopy.

FIG. 7 depicts an illustrative algorithm for colon cancer screening using FOBT (Fecal Occult Blood Testing), FLEX SIG (Flexible Sigmoidoscopy), and colonoscopy. If the member has no personal history of colon cancer or colonic adenomatous polyps 700, has had no prior colonoscopy in the past seven years 705, has a blood relative diagnosed at age X with colon cancer or colonic adenomatous polyps 710, and the member's age is greater than or equal to X–10 years 740, then HEALTHSCREEN will output a recommendation similar to the following recommendation 745: "Because of your family history of colon cancer or colonic adenomatous polyps, colonoscopy is recommended within the next one to three years. More information on this Preventative Medicine topic may be found at http://www.edoc4u.com/colonca.html."

If the member has no personal history of colon cancer or colonic adenomatous polyps 700, has had no prior colonoscopy within the past seven years 705, has a blood relative diagnosed at age X with colon cancer or colonic adenomatous polyps 710, and the member's age is not greater than or equal to X–10 years 740, and the member has had no prior fecal occult blood test (FOBT) in the last year 750, then HEALTHSCREEN will output a recommendation similar to the following recommendation 755: "Because of your family history of colon cancer or colonic adenomatous polyps, a fecal occult blood test (FOBT) is recommended one to three times within the next year. More information on this Preventative Medicine topic may be found at http://www.edoc4u.com/colonca.html."

If the member has no personal history of colon cancer or colonic adenomatous polyps 700, has had no prior colonoscopy in the past seven years 705, has no family history of colon cancer or colonic adenomatous polyps 710, is at least forty years old 715, is between forty and fifty years old 720, and has had no prior FOBT in the past one year 735, then HEALTHSCREEN will output a recommendation similar to the following recommendation 760: "Because of your risk for colon cancer or colonic adenomatous polyps, a fecal occult blood test (FOBT) is recommended one to three times within the next year. More information on this Preventative Medicine topic may be found at http://www.edoc4u.com/colonca.html."

If the member has no personal history of colon cancer or colonic adenomatous polyps 700, has had no prior colonoscopy in the past seven years 705, has no family history of colon cancer or colonic adenomatous polyps 710, is at least forty years old 715, is not between forty and fifty years old 720, and has had no prior flexible sigmoidoscopy in the last four years 725, then HEALTHSCREEN will output a recommendation similar to the following recommendation 730: "A screening flexible sigmoidoscopy (FLEX SIG) is recommended within the next year. More information on this Preventative Medicine topic may be found at http://www.edoc4u.com/colonca.html." Continuing the algorithm, if this member either has or has not had a FLEX SIG in the last 4 years 725, and has had no prior FOBT in the past one year 735, then HEALTHSCREEN will also output a recommendation similar to the following recommendation 760: "Because of your risk for colon cancer or colonic adenomatous polyps, a fecal occult blood test (FOBT) is recommended one to three times within the next year. More information on this Preventative Medicine topic may be found at http://www.edoc4u.com/colonca.html." Members not meeting the network-determined criteria receive no recommendations from this algorithm, and the HEALTHSCREEN processing continues.

Figure 8A:
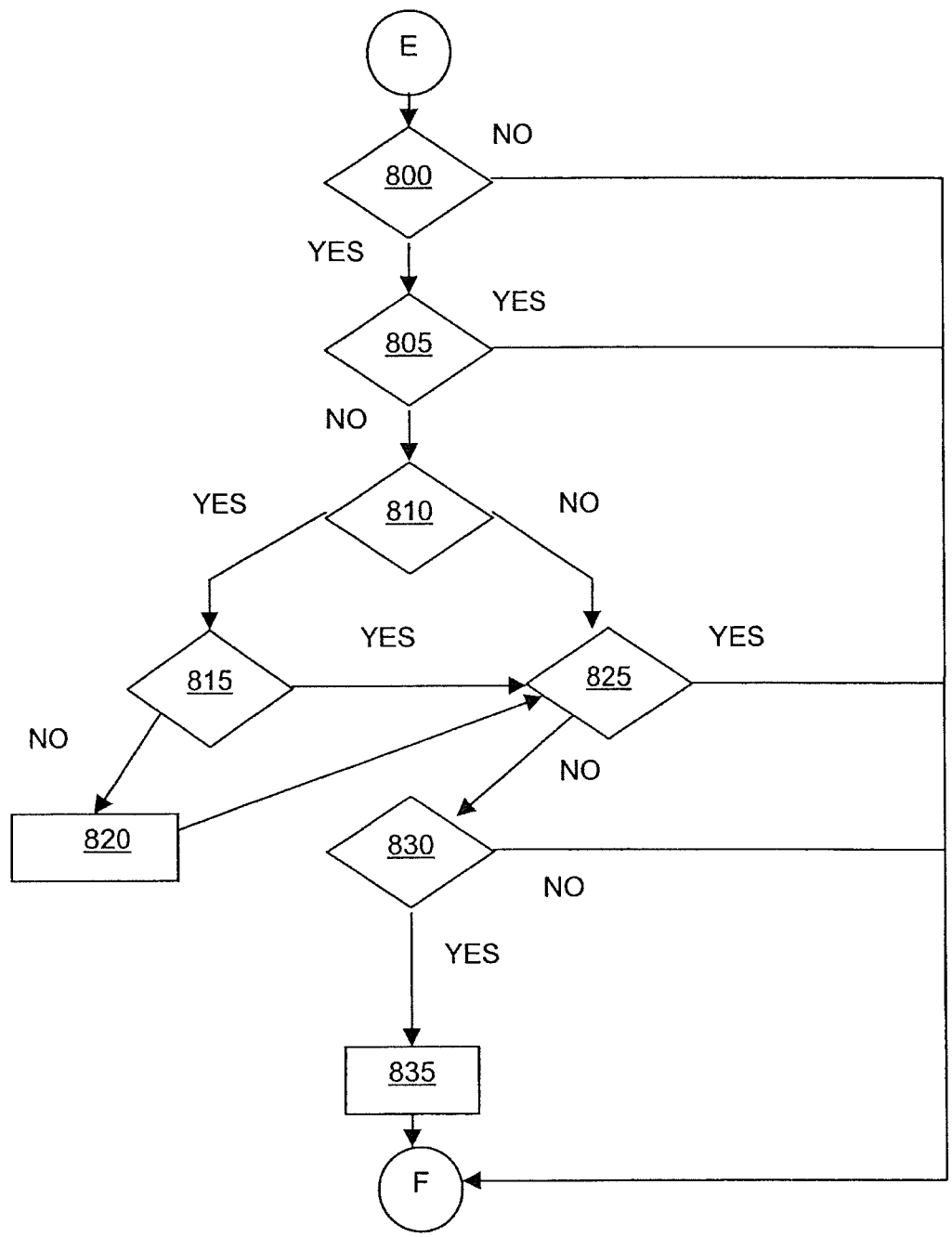
FIG. 8A depicts an algorithm for breast cancer screening using mammograms and breast cancer prevention using Tamoxifen.

FIG. 8A depicts an illustrative algorithm for breast cancer screening using mammograms and breast cancer prevention using Tamoxifen. If the member is female 800, has no personal history of breast cancer 805, has no family history of breast cancer 810, has not had a prior mammogram in the past year 825, and the member's age is at least thirty-five 830, then HEALTHSCREEN will output a recommendation similar to the following recommendation 835: "A routine mammogram is recommended within the next year. More information on this Preventative Medicine topic may be found at http://www.edoc4u/breastca.html."

If the member is female 800, has no personal history of breast cancer 805, has a positive family history of breast cancer 810, and is not currently taking Tamoxifen 815, then HEALTHSCREEN will output a recommendation similar to the following recommendation 820: "A discussion with your physician about the potential use of Tamoxifen to help prevent the development of breast cancer is recommended. More information on this Preventative Medicine topic may be found at http://www.edoc4u/tamoxifen.html." Continuing the algorithm, if this member is or is not taking Tamoxifen 815, has not had a prior mammogram in the past year 825, and the member's age is at least thirty-five 830, then HEALTHSCREEN will output a recommendation similar to the following recommendation 835: "A routine mammogram is recommended within the next year. More information on this Preventative Medicine topic may be found at http://www.edoc4u/breastca.html." Members not meeting the network-determined criteria receive no recommendations from this algorithm, and the HEALTHSCREEN processing continues.

Figure 8B:
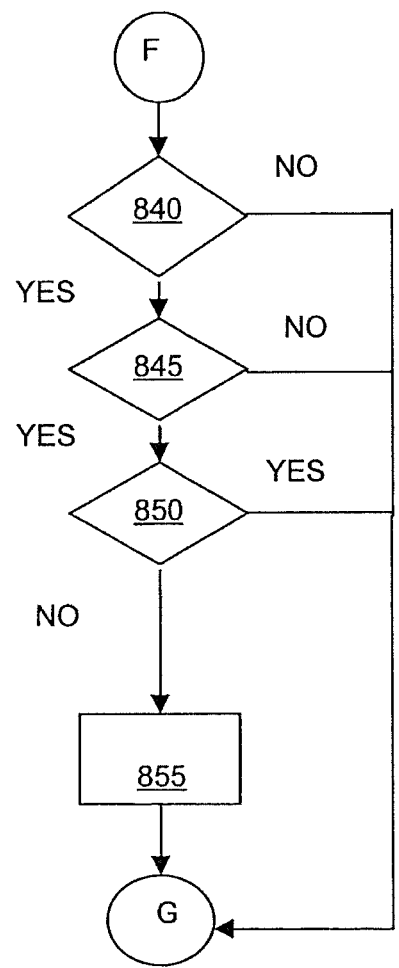
FIG. 8B depicts an algorithm for breast cancer screening using clinical breast examinations.

FIG. 8B depicts an illustrative algorithm for breast cancer screening using clinical breast examinations. If the member is female 840, over twenty-two years of age 845, and has not had a clinical breast examination in the last year 850, then HEALTHSCREEN will output a recommendation similar to the following recommendation 855: "A clinical breast examination by a qualified health care provider within the next year is recommended. More information on this Preventative Medicine topic may be found at http://www.edoc4u/breastca.html." Members not meeting the network determined criteria receive no recommendations from this algorithm, and the HEALTHSCREEN processing continues.

Figure 8C:
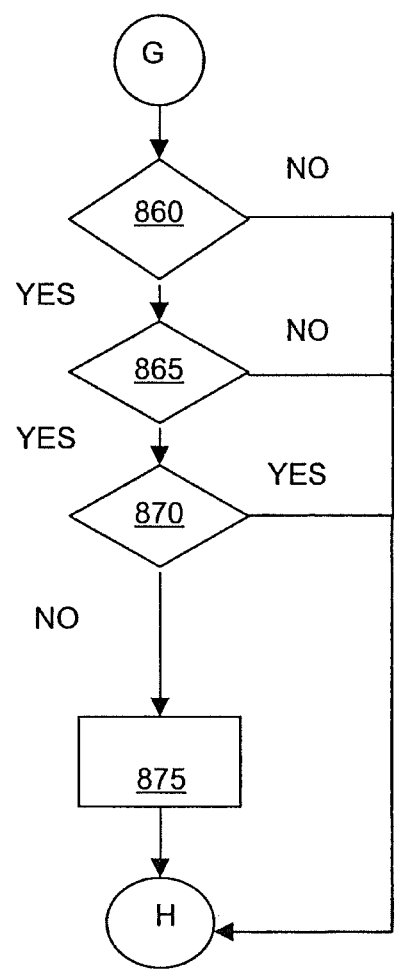
FIG. 8C depicts an algorithm for breast cancer screening using breast self-examinations.

FIG. 8C depicts an illustrative algorithm for breast cancer screening using breast self-examinations. If the member is female 860, over eighteen years of age 865, and not performing breast self-examination monthly 870, then HEALTHSCREEN will output a recommendation similar to the following recommendation 875: "A monthly self-breast examination is recommended each and every month. More information on this Preventative Medicine topic may be found at http://www.edoc4u/breastca.html." Members not meeting the network-determined criteria receive no recommendations from this algorithm, and the HEALTHSCREEN processing continues.

Figure 9:
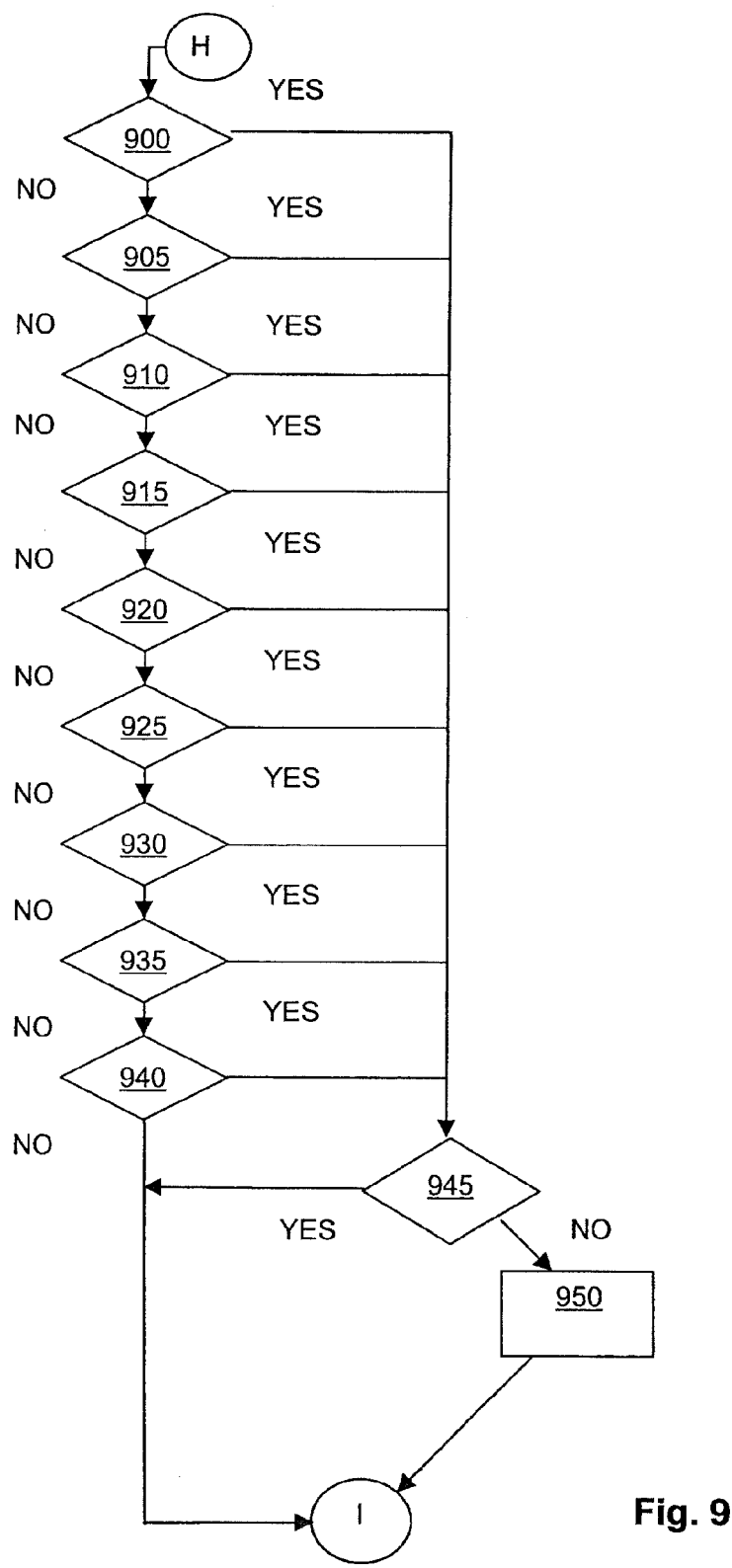
FIG. 9 depicts an algorithm for coronary artery disease (CAD) prevention using cholesterol surveillance.

FIG. 9 depicts an illustrative algorithm for coronary artery disease (CAD) prevention using cholesterol surveillance. If the member has hypertension 900 and has had no cholesterol check in the past year 945, then HEALTHSCREEN will output a recommendation similar to the following recommendation 950: "A fasting blood cholesterol level is recommended within the next year."

If the member has CAD 905 and has had no cholesterol check in the past year 945, then HEALTHSCREEN will output a recommendation similar to the following recommendation 950: "A fasting blood cholesterol level is recommended within the next year."

If the member is a smoker 910 and has had no cholesterol check in the past year 945, then HEALTHSCREEN will output a recommendation similar to the following recommendation 950: "A fasting blood cholesterol level is recommended within the next year."

If the member has diabetes 915 and has had no cholesterol check in the past year 945, then HEALTHSCREEN will output a recommendation similar to the following recommendation 950: "A fasting blood cholesterol level is recommended within the next year."

If the member is over forty-four years of age 920 and has had no cholesterol check in the past year 945, then HEALTHSCREEN will output a recommendation similar to the following recommendation 950: "A fasting blood cholesterol level is recommended within the next year."

If the member has high cholesterol 925 and has had no cholesterol check in the past year 945, then HEALTHSCREEN will output a recommendation similar to the following recommendation 950: "A fasting blood cholesterol level is recommended within the next year."

If the member has a family history of CAD 930 and has had no cholesterol check in the past year 945, then HEALTHSCREEN will output a recommendation similar to the following recommendation 950: "A fasting blood cholesterol level is recommended within the next year."

If the member takes medications for cholesterol 935 and has had no cholesterol check in the past year 945, then HEALTHSCREEN will output a recommendation similar to the following recommendation 950: "A fasting blood cholesterol level is recommended within the next year."

If the member has a family history of stroke 940 and has had no cholesterol check in the past year 945, then HEALTHSCREEN will output a recommendation similar to the following recommendation 950: "A fasting blood cholesterol level is recommended within the next year." With each recommendation generated from this algorithm, HEALTHSCREEN will also output, "More information on this Preventative Medicine topic may be found at http://www.edoc4u/cad.html." Members not meeting the network-determined criteria receive no recommendations from this algorithm, and the HEALTHSCREEN processing continues.

Figure 10:
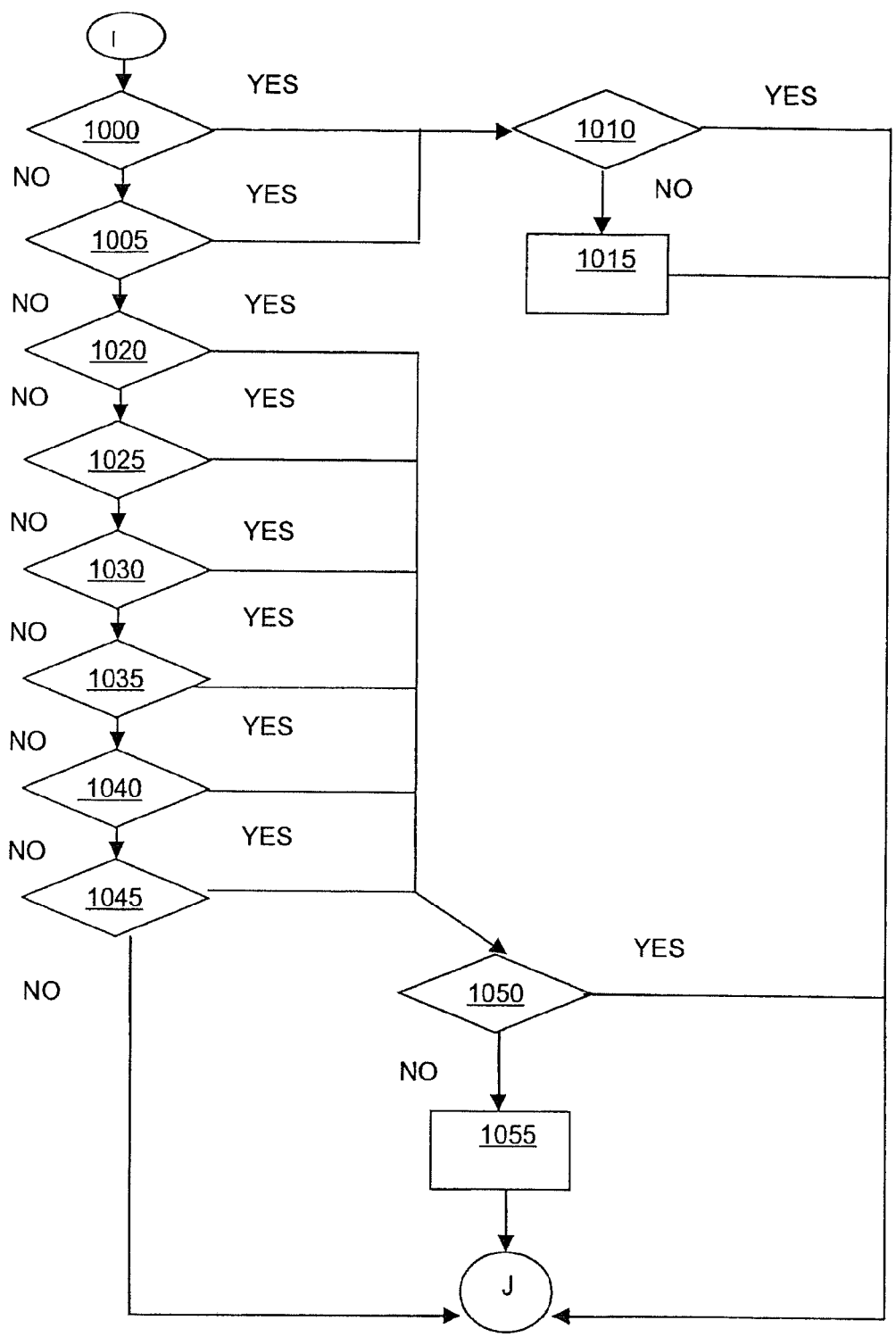
FIG. 10 depicts an algorithm for surveillance of existing hypertension using five-day blood pressure checks and for hypertension screening using routine blood pressure checks.

FIG. 10 depicts an illustrative algorithm for surveillance of existing hypertension using five-day blood pressure checks and for hypertension screening using routine blood pressure checks. If the member has hypertension 1000 OR takes medications for hypertension 1005, and has not had a five-day blood pressure check in the past year 1010, then HEALTHSCREEN will output a recommendation similar to the following recommendation 1015: "A five-day blood pressure check is recommended within the next year to monitor your blood pressure. More information on this Preventative Medicine topic may be found at http://www.edoc4u/htn.html."

If the member does not have hypertension 1000 or take medications for hypertension 1005, then algorithm screens for the presence of a least one of the following criteria: coronary artery disease (CAD) 1020, diabetes 1025, a family history of high blood pressure 1030, a family history of coronary artery disease 1035, smoking 1040, or age greater than twenty-two 1045. If at least one of the preceding five criteria is present and the member has not had a routine blood pressure check in the last year 1050, then HEALTHSCREEN will output a recommendation similar to the following recommendation 1055: "A routine blood pressure measurement by a qualified health care provider is recommended this year.

More information on this Preventative Medicine topic may be found at http://www.edoc4u/htn.html." Members not meeting the network-determined criteria receive no recommendations from this algorithm, and the HEALTHSCREEN processing continues.

Figure 11:
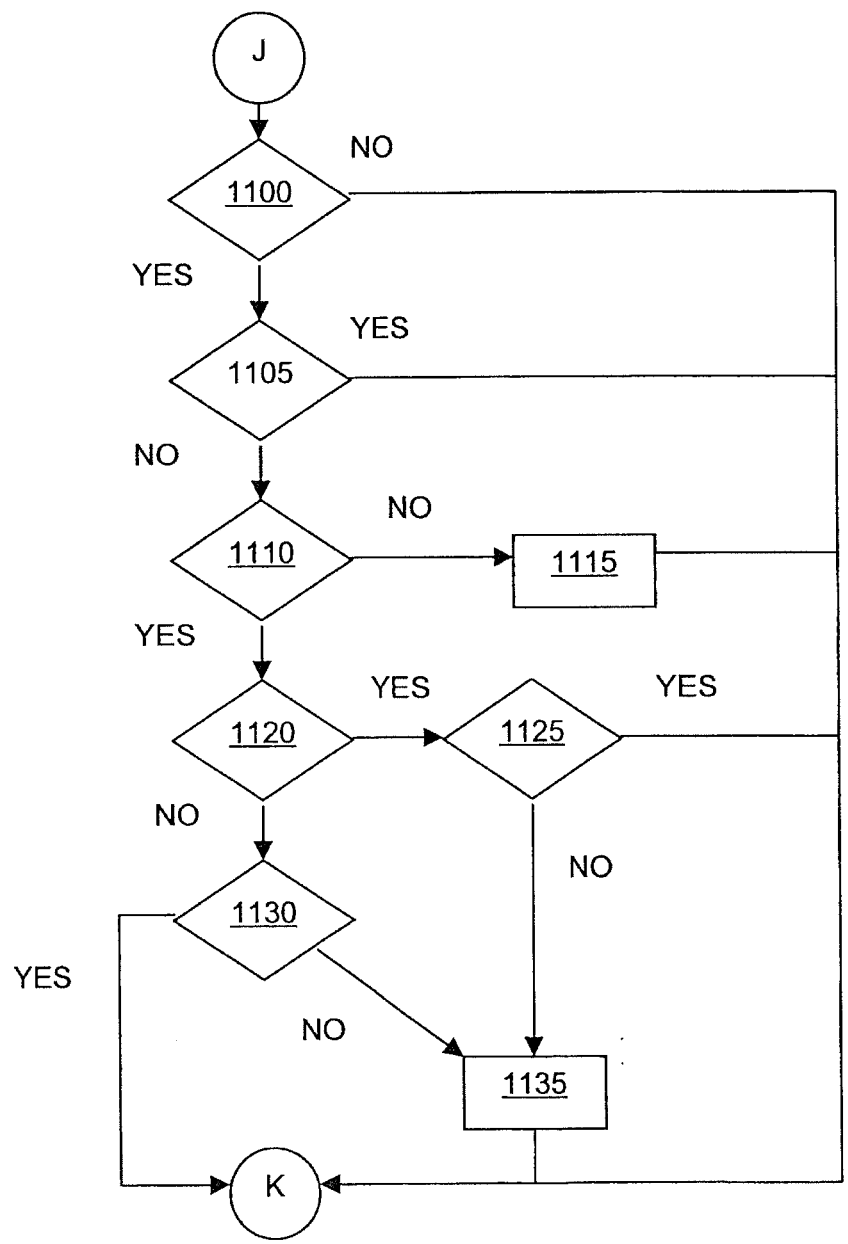
FIG. 11 depicts an algorithm for prevention of cervical cancer using Pap smears and pelvic examinations.

FIG. 11 depicts an illustrative algorithm for prevention of cervical cancer using Pap smears and pelvic examinations. If member is female 1100, has no personal history of cervical cancer 1105, had a normal result on her last Pap smear 1110, has not had a hysterectomy 1120, and has not had a Pap smear in the past year 1130, then HEALTHSCREEN will output a recommendation similar to the following recommendation 1135: "A Pap smear and pelvic examination are recommended within the next year. More information on this Preventative Medicine topic may be found at http://www.edoc4u/cervca.html."

If the member is female 1100, has no personal history of cervical cancer 1105, had a normal result on her last Pap smear 1110, has had a hysterectomy 1120, and has had no Pap smear in the past 2 years 1125, then HEALTHSCREEN will output a recommendation similar to the following recommendation 1135: "A Pap smear and pelvic examination are recommended within the next year. More information on this Preventative Medicine topic may be found at http://www.edoc4u/cervca.html."

If the member is female 1100, has no personal history of cervical cancer 1105, and her last Pap smear was NOT normal 1110, then HEALTHSCREEN will output a recommendation similar to the following recommendation 1115: "Because of your history of an abnormal Pap smear, please discuss your specific interval for Pap smears and pelvic examinations with your health care provider as soon as possible." Members not meeting the network-determined criteria receive no recommendations from this algorithm, and the HEALTHSCREEN processing continues.

Figure 12:
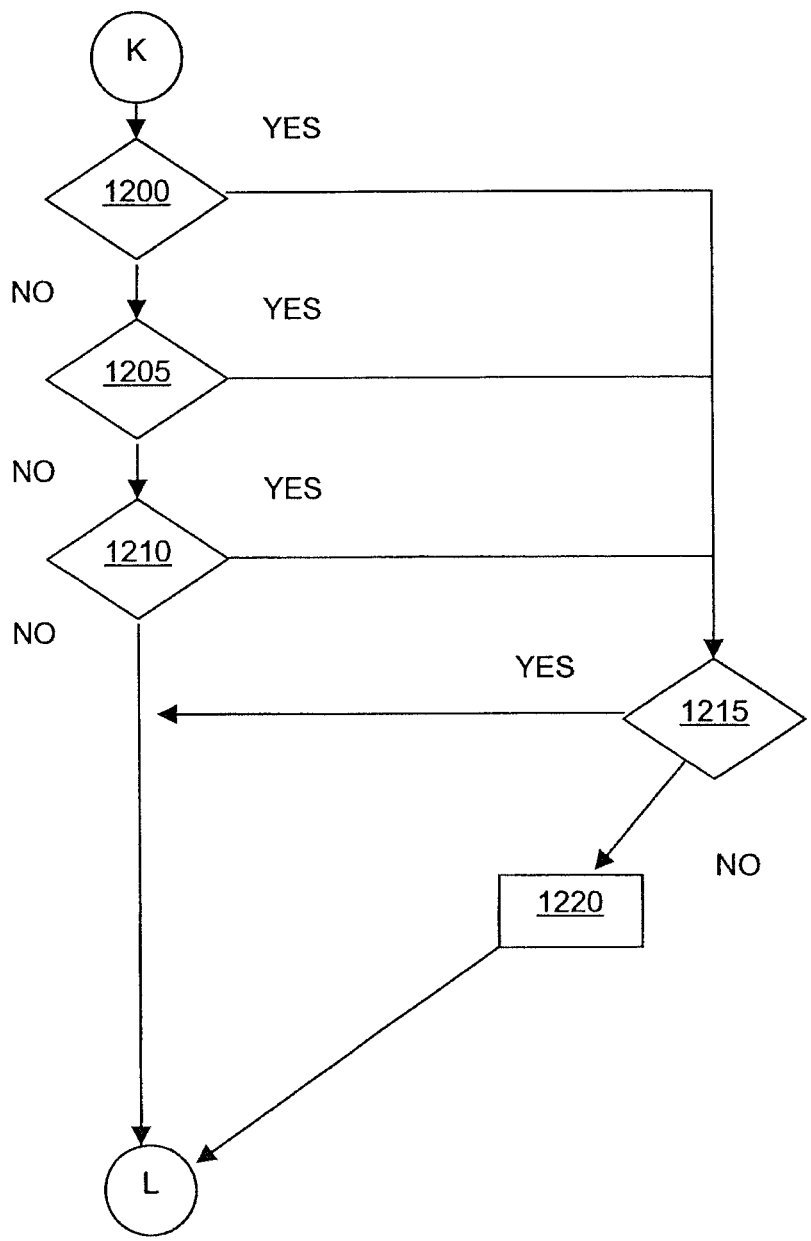
FIG. 12 depicts an algorithm of screening for thyroid disease using Thyroid Stimulating Hormone levels (TSH).

FIG. 12 depicts an illustrative algorithm for thyroid disease screening using Thyroid Stimulating Hormone levels (TSH). If the member has a family history of thyroid disease 1200, a personal history of thyroid disease 1205, or is more than fifty-nine years old 1210, and the member has not had a TSH blood level in the past year 1215, then HEALTHSCREEN will output a recommendation similar to the following recommendation 1220: "A blood thyroid level (TSH) is recommended within the next year. More information on this Preventative Medicine topic may be found at http://www.edoc4u/thyroid.html." Members not meeting the network-determined criteria receive no recommendations from this algorithm, and the HEALTHSCREEN processing continues.

Figure 13:
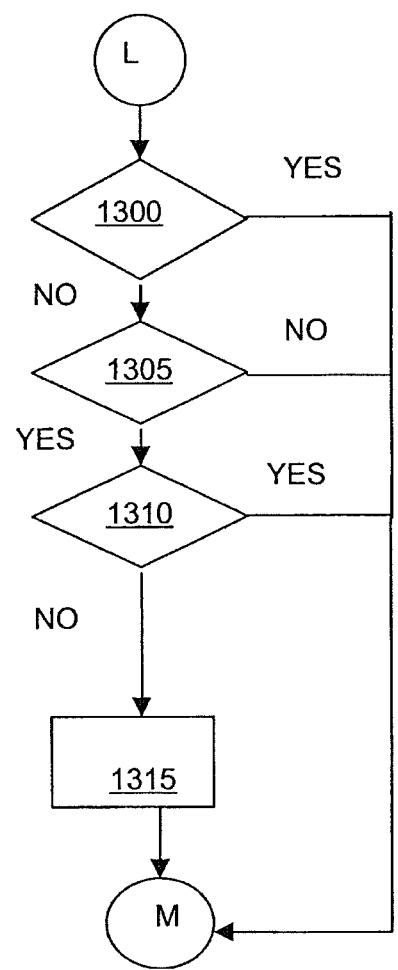
FIG. 13 depicts an algorithm of screening for gastric cancer using *Helicobacter Pylori* antibody testing.

FIG. 13 depicts an illustrative algorithm for gastric cancer screening using *Helicobacter Pylori* antibody testing. If the member has no personal history of gastric cancer 1300, has a family history of gastric cancer 1305, and has not had a *Helicobacter Pylori* antibody test 1310, then HEALTHSCREEN will output a recommendation similar to the following recommendation 1315: "A *Helicobacter Pylori* antibody blood test is recommended to determine whether you may have cancer-causing bacteria present in your stomach. More information on this Preventative Medicine topic may be found at http://www.edoc4u/gastca.html." Members not meeting the network-determined criteria receive no recommendations from this algorithm, and the HEALTHSCREEN processing continues.

Figure 14A:
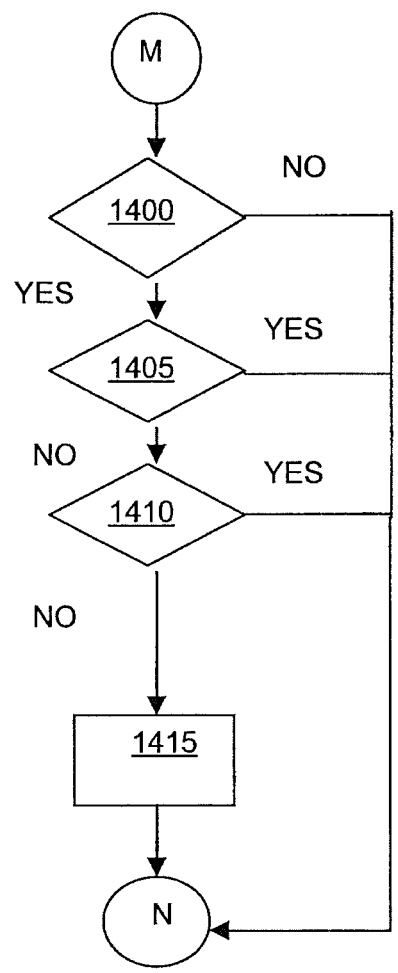
FIG. 14A depicts an algorithm of screening for testicular cancer using clinical testicular examinations.

FIG. 14A depicts an illustrative algorithm for testicular cancer screening using clinical testicular examinations. If the member is male 1400, has no personal history of testicular cancer 1405, and has not had a clinical testicular examination in the past 2 years 1410, then HEALTHSCREEN will output a recommendation similar to the following recommendation 1415, "Clinical testicular examination by a qualified health care provider is recommended within the next year. More information on this Preventative Medicine topic may be found at http://www.edoc4u/testca.html." Members not meeting the network-determined criteria receive no recommendations from this algorithm, and the HEALTHSCREEN processing continues.

Figure 14B:
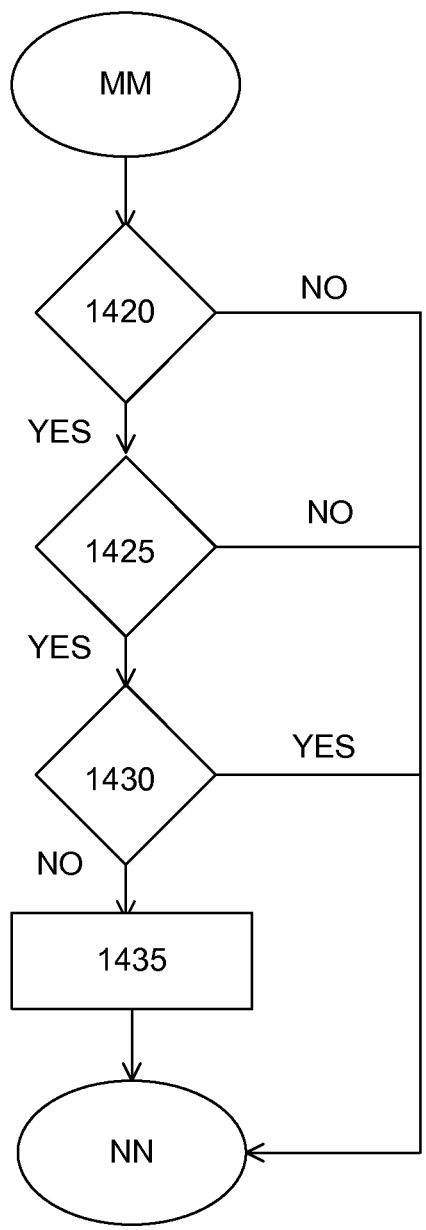
FIG. 14B depicts an algorithm of screening for testicular cancer using testicular self-examinations.

FIG. 14B depicts an illustrative algorithm for testicular cancer screening using testicular self-examinations. If the member is male 1420, at least eighteen years old 1425, and has not been performing testicular self-examination 1430, then HEALTHSCREEN will output a recommendation similar to the following recommendation 1435: "Testicular self-examination is recommended each month to detect possible testicular cancer. More information on this Preventative Medicine topic may be found at http://www.edoc4u/testca.html." Members not meeting the network-determined criteria receive no recommendations from this algorithm, and the HEALTHSCREEN processing continues.

Figure 15:
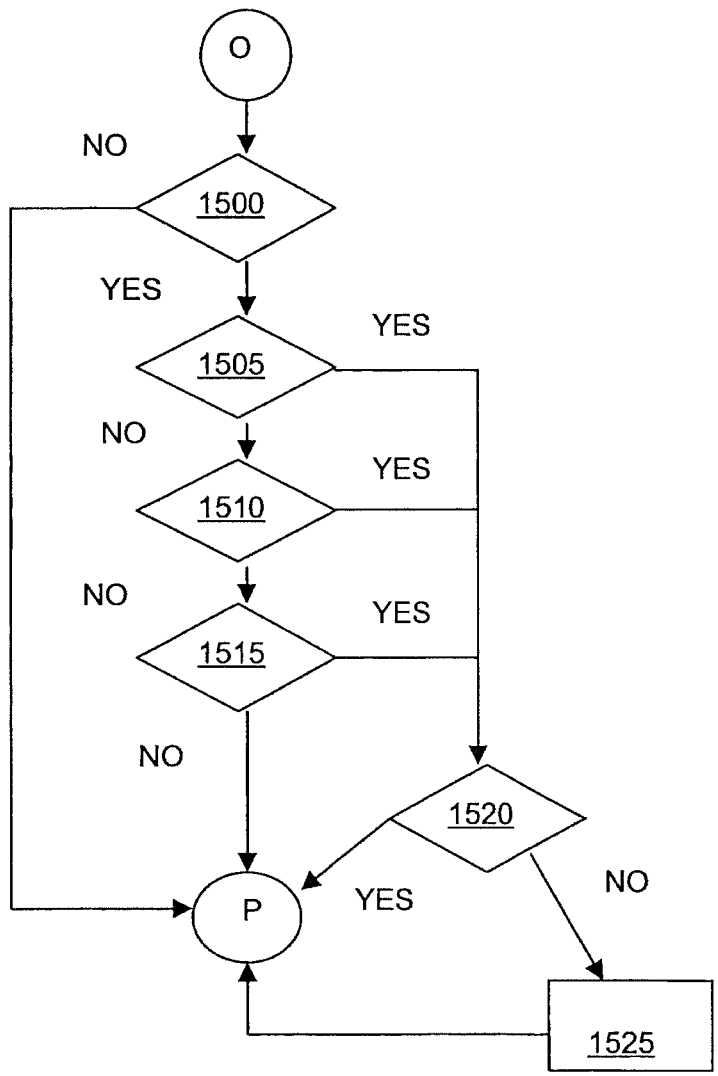
FIG. 15 depicts an algorithm of screening for glaucoma using eye examination and intraocular pressure measurement.

FIG. 15 depicts an illustrative algorithm for glaucoma screening using eye examination and intraocular pressure measurement. If the member is male 1500, has a personal history of glaucoma 1505 or a family history of glaucoma 1510 or is African-American 1515, and has not had an eye examination with intraocular pressure measurement in the past two years 1520, then HEALTHSCREEN will output a recommendation similar to the following recommendation 1525: "Eye examination with intraocular pressure measurements is recommended within the next year. More information on this Preventative Medicine topic may be found at http://www.edoc4u/glaucoma.html." Members not meeting the network-determined criteria receive no recommendations from this algorithm, and the HEALTHSCREEN processing continues.

Figure 16:
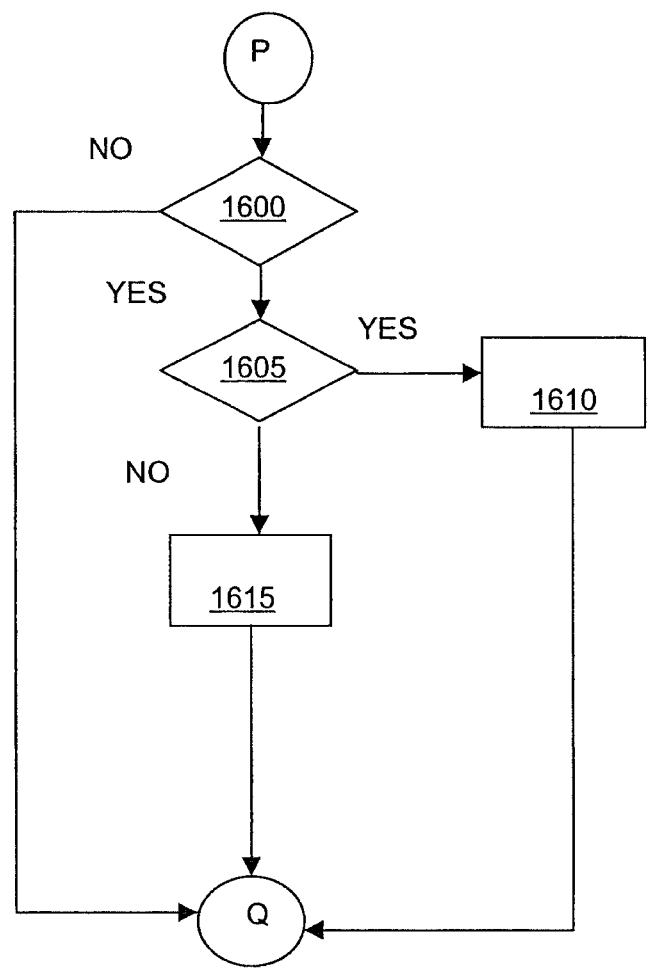
FIG. 16 depicts an algorithm of screening for inactivity using questions regarding exercise habits.

FIG. 16 depicts an illustrative algorithm for physical inactivity screening using questions regarding exercise habits. If the member exercises less than three times per week 1600 and does not have a personal history of coronary artery disease 1605, then HEALTHSCREEN will output a recommendation similar to the following recommendation 1615: "An aerobic exercise program in which your heart rate maintains within a range of 50-75% of your maximal heart rate (MHR, defined as 225—your age), for twenty minutes at least three times a week is recommended. This type of program will provide lasting health benefits and minimize future risk of cardiovascular disease. More information on this Preventative Medicine topic may be found at http://www.edoc4u/exercise.html." If the member exercises less than three times per week 1600 and has a personal history of coronary artery disease 1605, then HEALTHSCREEN will output a recommendation similar to the following recommendation 1610: "Because of your personal history of coronary artery disease (CAD), please formulate an exercise plan with your personal physician as exercise will improve your functional status." Members not meeting the network-determined criteria receive no recommendations from this algorithm, and the HEALTHSCREEN processing continues.

Figure 17:
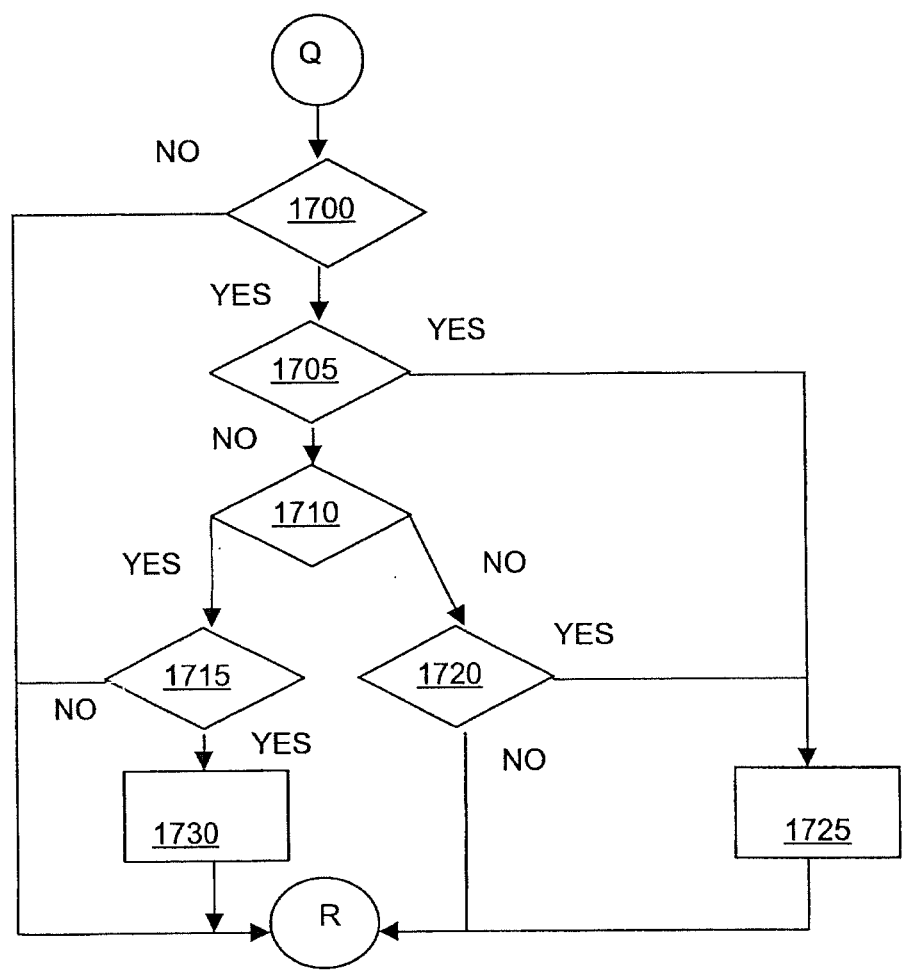
FIG. 17 depicts an algorithm for initiation of a new exercise program and the potential pre-exercise work-up required.

FIG. 17 depicts an illustrative algorithm for initiation of a new exercise program and the potential pre-exercise work-up required. If the member plans to initiate a new exercise program 1700, has no personal history of coronary artery disease (CAD) 1705, is male 1710, and is at least forty years old 1715, then HEALTHSCREEN will output a recommendation similar to the following recommendation 1730: "Because of the potential for exertional stress to the heart from a new exercise program, a baseline electrocardiogram (EKG) and routine physical examination are recommended prior to starting the exercise program. More information on this Preventative Medicine topic may be found at http://www.edoc4u/exercise.html."

If the member plans to initiate a new exercise program 1700, has no personal history of coronary artery disease (CAD) 1705, is not male 1710, and is at least fifty years old 1720, then HEALTHSCREEN will output a recommendation similar to the following recommendation 1725: "Because of the potential for exertional stress to the heart from a new exercise program, a baseline electrocardiogram (EKG) and routine physical examination are recommended prior to starting the exercise program. More information on this Preventative Medicine topic may be found at http://www.edoc4u/exercise.html."

If the member plans to initiate a new exercise program 1700, and has a personal history of coronary artery disease (CAD) 1705, then HEALTHSCREEN will output a recommendation similar to the following recommendation 1725: "Because of the potential for exertional stress to the heart from a new exercise program, a baseline electrocardiogram (EKG) and routine physical examination are recommended prior to starting the exercise program. More information on this Preventative Medicine topic may be found at http://www.edoc4u/exercise.html." Members not meeting the network-determined criteria receive no recommendations from this algorithm, and the HEALTHSCREEN processing continues.

Figure 18:
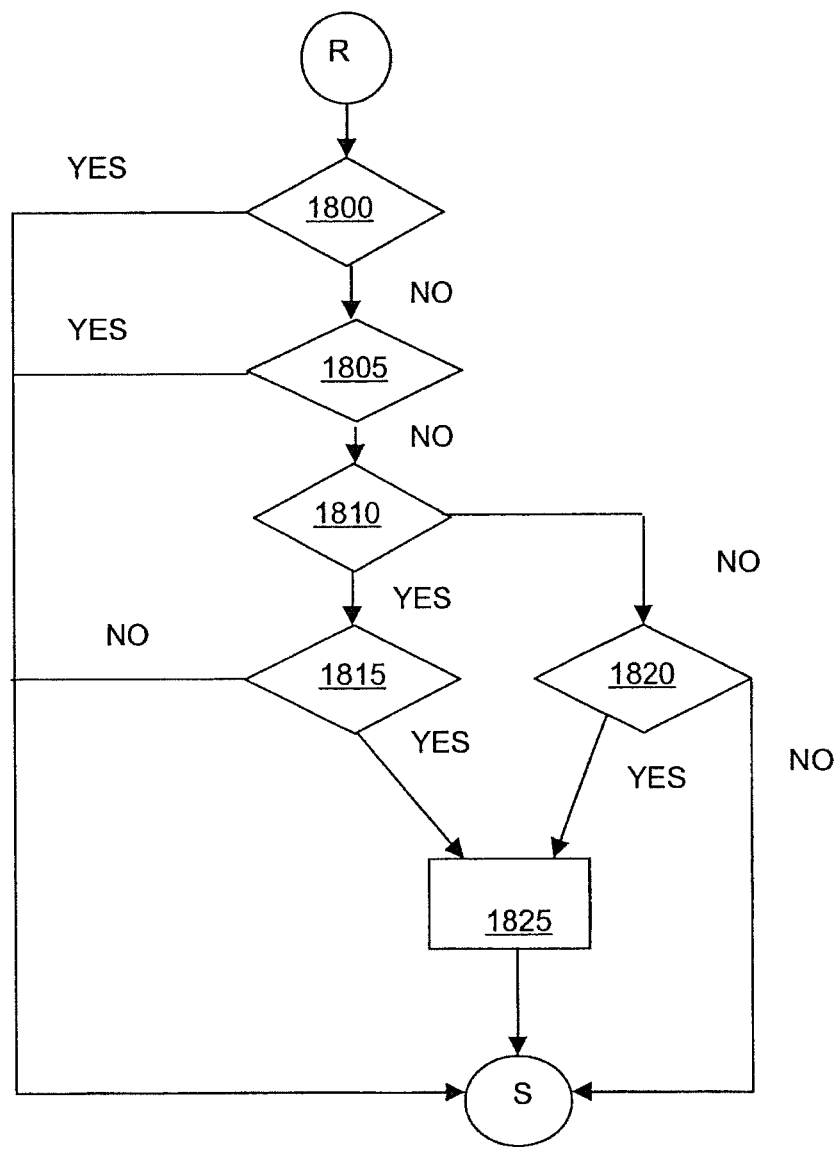
FIG. 18 depicts an algorithm for screening for CAD using exercise treadmill testing.

FIG. 18 depicts an illustrative algorithm for CAD screening using exercise treadmill testing. If the member has not had a prior exercise treadmill test 1800, has no personal history coronary artery disease 1805, and is male 1810, the algorithm screens for the presence of at least two of the following six risk factors 1815: age at least forty-five, current smoker, family history of heart attack, personal history of hypertension, personal history of diabetes, and personal history of high cholesterol. If at least two of the preceding six risk factors are present, then HEALTHSCREEN will output a recommendation similar to the following recommendation 1825: "Based on your current risk factors for heart disease, an exercise Treadmill test within the next year should be completed to identify underlying coronary artery disease (CAD). If you are unable to walk on a treadmill or know that you have electrocardiogram (EKG) abnormalities, then other similar tests, such as a nuclear medicine thallium scan, an electron beam Cat Scan, or a stress echo test may be best for you. More information on this Preventative Medicine topic may be found at http://www.edoc4u/cad.html." Members not meeting the network-determined criteria receive no recommendations from this algorithm, and the HEALTHSCREEN processing continues.

If the member has not had a prior exercise treadmill test 1800, has no personal history of coronary artery disease 1805, is not male 1810, the algorithm screens for the presence of at least two of the following six risk factors 1820: age at least fifty-five, current smoker, family history of heart attack, personal history of hypertension, personal history of diabetes, and personal history of high cholesterol. If at least two of the preceding six risk factors are present, then HEALTHSCREEN will output a recommendation similar to the following recommendation 1825: "Based on your current risk factors for heart disease, an exercise Treadmill test within the next year should be completed to identify underlying coronary artery disease (CAD). If you are unable to walk on a treadmill or know that you have electrocardiogram (EKG) abnormalities, then other similar tests, such as a nuclear medicine thallium scan, an electron beam Cat Scan, or a stress echo test may be best for you. More information on this Preventative Medicine topic may be found at http://www.edoc4u/cad.html." Members not meeting the network-determined criteria receive no recommendations from this algorithm, and the HEALTHSCREEN processing continues.

Figure 19:
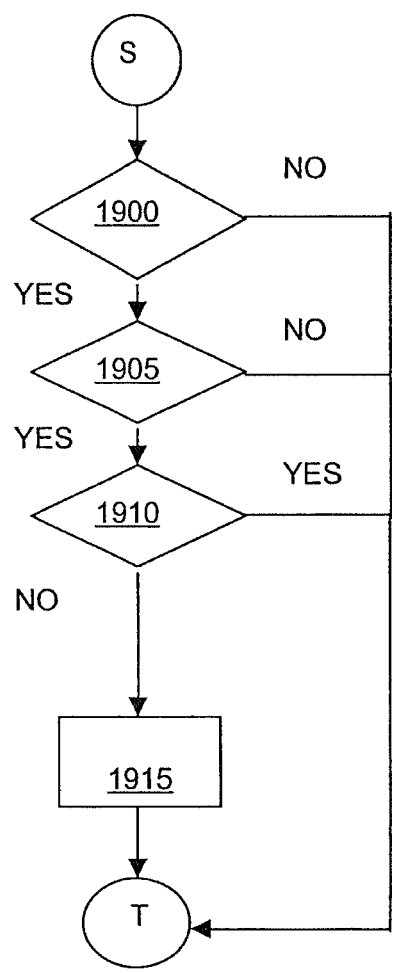
FIG. 19 depicts an algorithm for screening for iron deficiency anemia using complete blood counts.

FIG. 19 depicts an illustrative algorithm for screening for iron deficiency anemia using complete blood counts. If the member is female 1900, has a heavy flow during her monthly menstrual cycle 1905, and has not had a blood count check in the past year 1910, then HEALTHSCREEN will output a recommendation similar to the following recommendation 1915: "Because of the possibility of iron deficiency anemia from menstrual blood losses, a blood count is recommended to determine if iron supplementation is necessary. More information on this Preventative Medicine topic may be found at http://www.edoc4u/anemia.html." Members not meeting the network-determined criteria receive no recommendations from this algorithm, and the HEALTHSCREEN processing continues.

Figure 20:
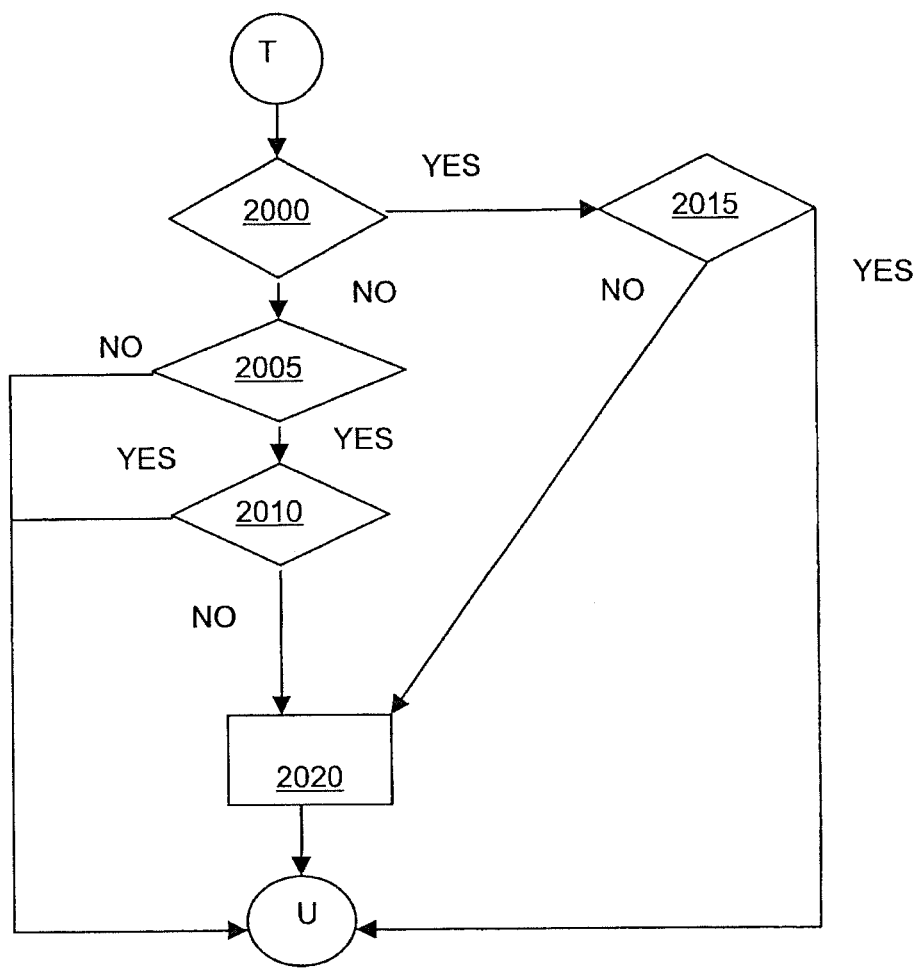
FIG. 20 depicts an algorithm for screening for hearing deficits using a routine hearing examination.

FIG. 20 depicts an illustrative algorithm for screening for hearing deficits using a routine hearing examination. If the member engages in an occupation or activity with extreme noise exposure 2000 and has had no hearing test in the past two years 2015, then HEALTHSCREEN will output a recommendation similar to the following recommendation 2020: "A routine hearing test is recommended within the next year to monitor the baseline level of hearing acuity and identify any potential hearing deficits. More information on this Preventative Medicine topic may be found at http://www.edoc4u/hearing.html." If the member does not engage in an occupation or activity with extreme noise exposure 2000, is at least sixty years old 2005, and has had no hearing test in past four years 2010, then HEALTHSCREEN will output a recommendation similar to the following recommendation 2020: "A routine hearing test is recommended within the next year to monitor the baseline level of hearing acuity and identify any potential hearing deficits. More information on this Preventative Medicine topic may be found at http://www.edoc4u/hearing.html." Members not meeting the network-determined criteria receive no recommendations from this algorithm, and the HEALTHSCREEN processing continues.

Figure 21:
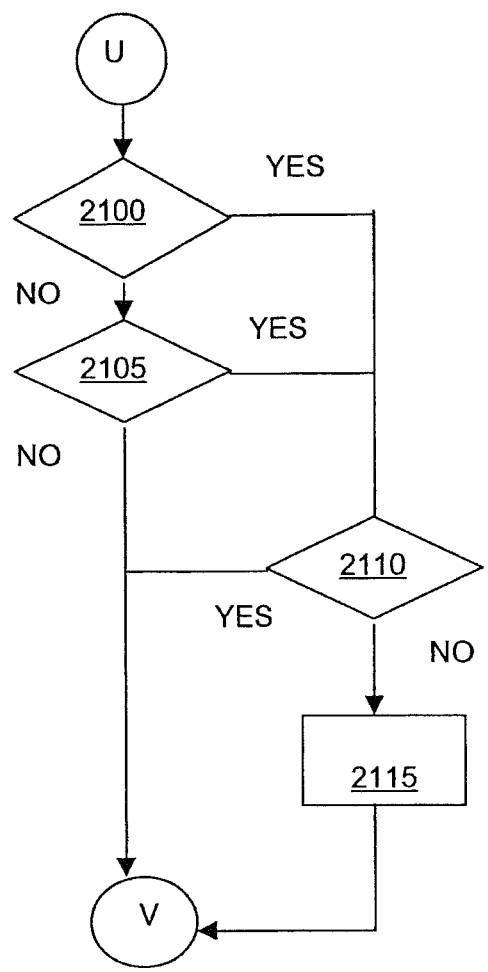
FIG. 21 depicts an algorithm for screening for retinal eye disease using full retinal eye examination by an ophthalmologist.

FIG. 21 depicts an illustrative algorithm for screening for retinal eye disease using full retinal eye examination by an ophthalmologist. If the member has a personal history of diabetes 2100 or hypertension 2105 and has not had a full retinal eye examination in the last year 2110, then HEALTHSCREEN will output a recommendation similar to the following recommendation 2115: "An eye examination of the retina by a qualified ophthalmologist is recommended within the next year to identify early retinal disease which could lead to blindness. More information on this Preventative Medicine topic may be found at http://www.edoc4u/vision.html." Members not meeting the network-determined criteria receive no recommendations from this algorithm, and the HEALTHSCREEN processing continues.

Figure 22:
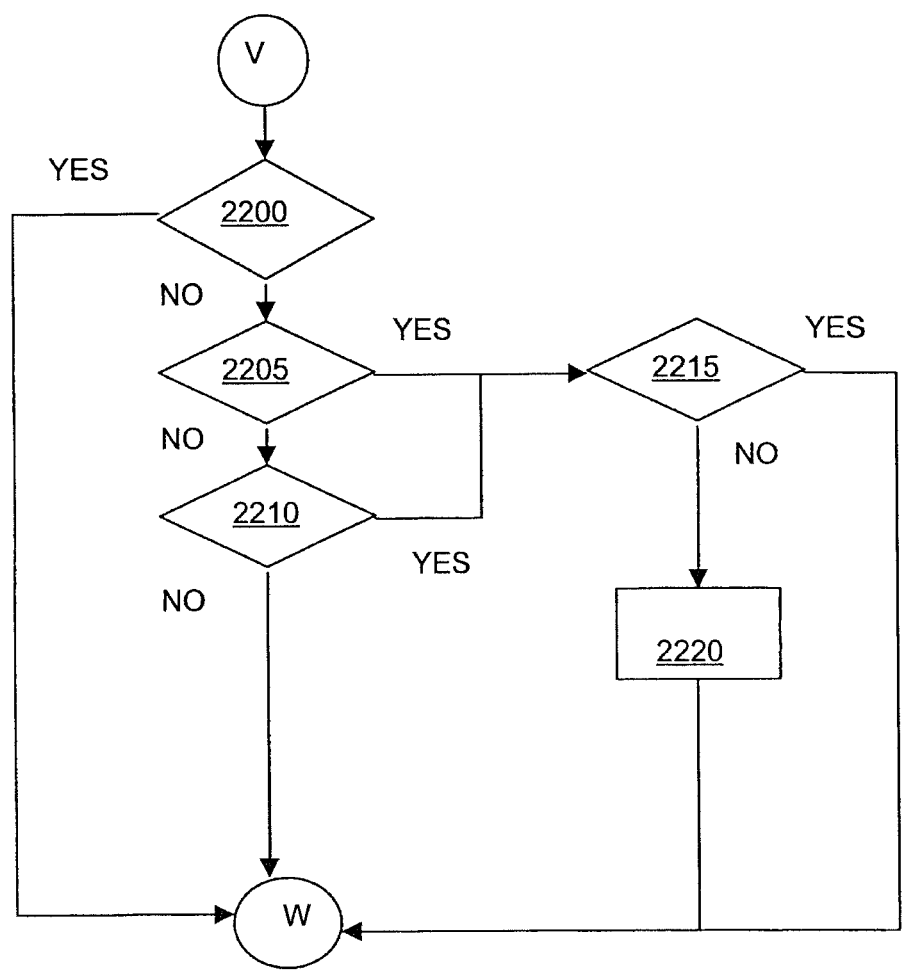
FIG. 22 depicts an algorithm for screening for diabetes using fasting blood glucose levels.

FIG. 22 depicts an illustrative algorithm for screening for diabetes using fasting blood glucose levels. If the member has no personal history of diabetes 2200, has had diabetes of pregnancy 2205 or a family history of diabetes 2210, and has not had a fasting blood glucose check in last year 2215, then HEALTHSCREEN will output a recommendation similar to the following recommendation 2220: "A fasting blood glucose check is recommended within the next year to screen for diabetes." More information on this Preventative Medicine topic may be found at http://www.edoc4u/diabetes.html."

Members not meeting the network-determined criteria receive no recommendations from this algorithm, and the HEALTHSCREEN processing continues.

Figure 23:
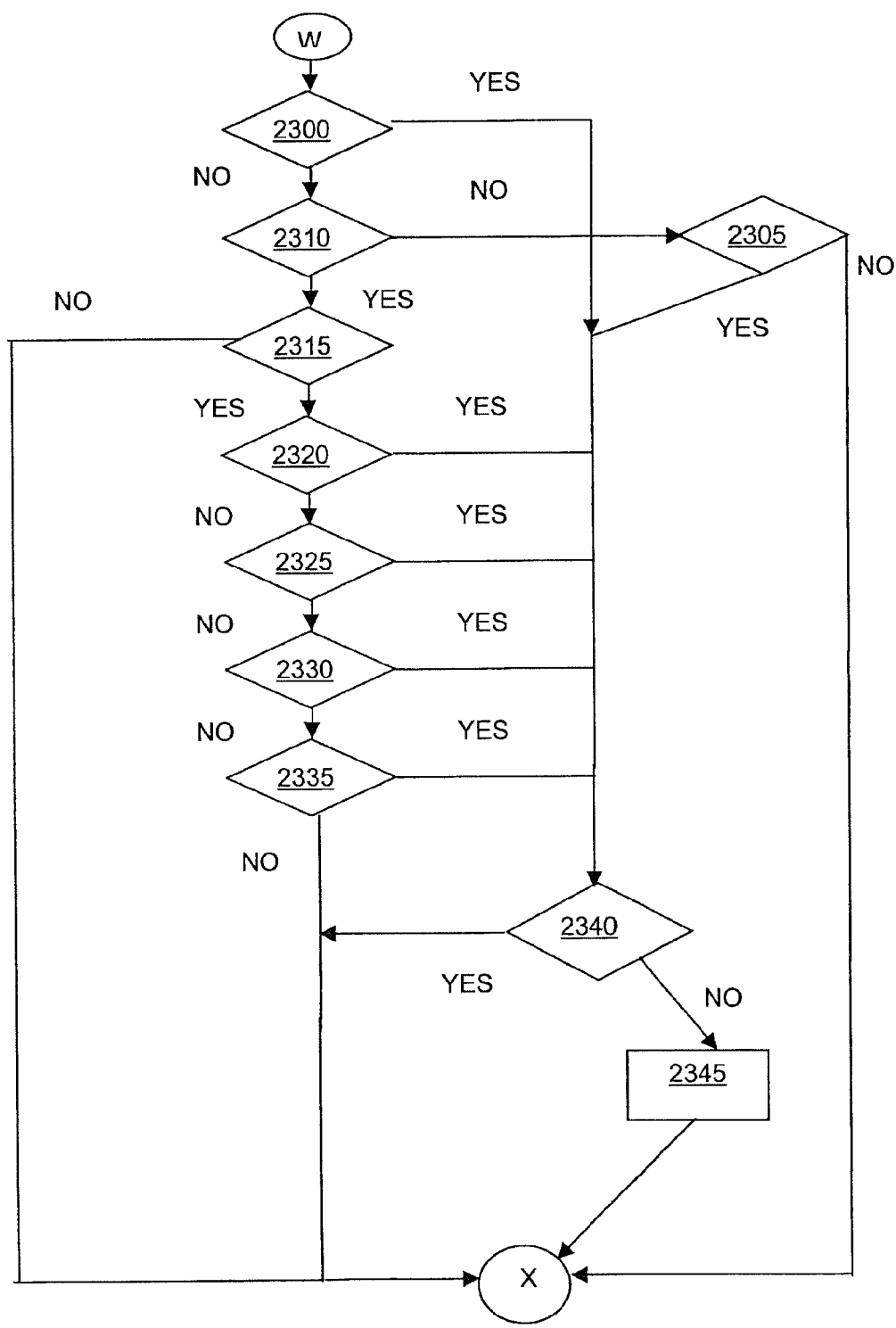
FIG. 23 depicts an algorithm for screening for osteoporosis using Dual Energy X-Ray Absorptiometry (DXA) Scans to measure bone density.

FIG. 23 depicts an illustrative algorithm for screening for osteoporosis using Dual Energy X-Ray Absorptiometry Scans (DXA-Scans) to measure bone density. If a member is taking prednisone 2300 and has not had a DXA-Scan 2340, then HEALTHSCREEN will output a recommendation similar to the following recommendation 2345: "An evaluation of your bone density with a DXA-Scan or comparable scanner is recommended within the next year to assess the risk for future osteoporotic fractures."

If the member is male 2310, is hypogonadal 2305, and has not had a DXA-Scan 2340, then HEALTHSCREEN will output a recommendation similar to the following recommendation 2345: "An evaluation of your bone density with a DXA-Scan or comparable scanner is recommended within the next year to assess the risk for future osteoporotic fractures."

If the member is not male 2310, is postmenopausal 2315, is Caucasian 2320 or Asian 2325 or has a personal history of vertebral fractures/osteoporosis 2330 or a family history of vertebral fractures/osteoporosis 2335, and has never had a DXA-Scan 2340, then HEALTHSCREEN will output a recommendation similar to the following recommendation 2345: "An evaluation of your bone density with a DXA-Scan or comparable scanner is recommended within the next year to assess the risk for future osteoporotic fractures." With each recommendation generated from this algorithm, HEALTHSCREEN will also output, "More information on this Preventative Medicine topic may be found at http://www.edoc4u/bones.html." Members not meeting the network-determined criteria receive no recommendations from this algorithm, and the HEALTHSCREEN processing continues.

Figure 24A:
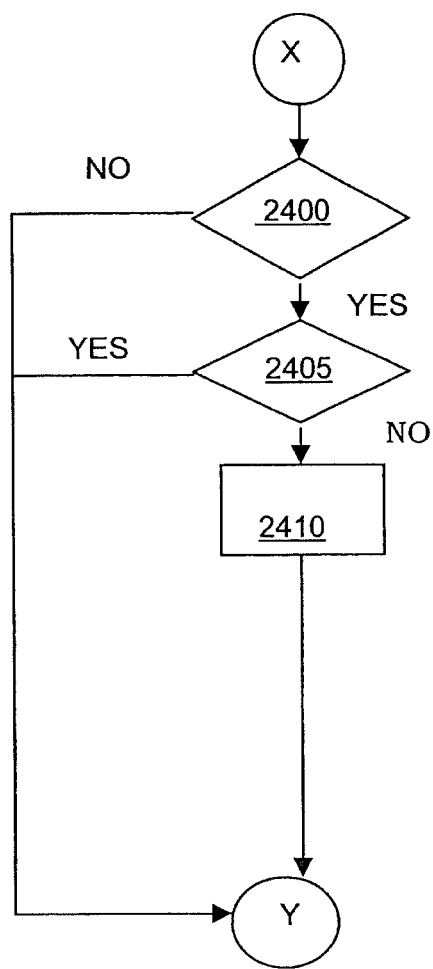
FIG. 24A depicts an algorithm for screening for diabetic neuropathy or foot infection using routine diabetic foot examination.

FIG. 24A depicts an illustrative algorithm for screening for diabetic neuropathy or foot infection using routine diabetic foot examination. If the member has a personal history of diabetes 2400 and has not had a foot examination in the past year 2405, then HEALTHSCREEN will output a recommendation similar to the following recommendation 2410: "Because of your diabetes, a foot examination by a qualified health care provider is recommended within the next year to evaluate for diabetic neuropathy or infection. More information on this Preventative Medicine topic may be found at http://www.edoc4u/diabetes.html." Members not meeting the network-determined criteria receive no recommendations from this algorithm, and the HEALTHSCREEN processing continues.

Figure 24B:
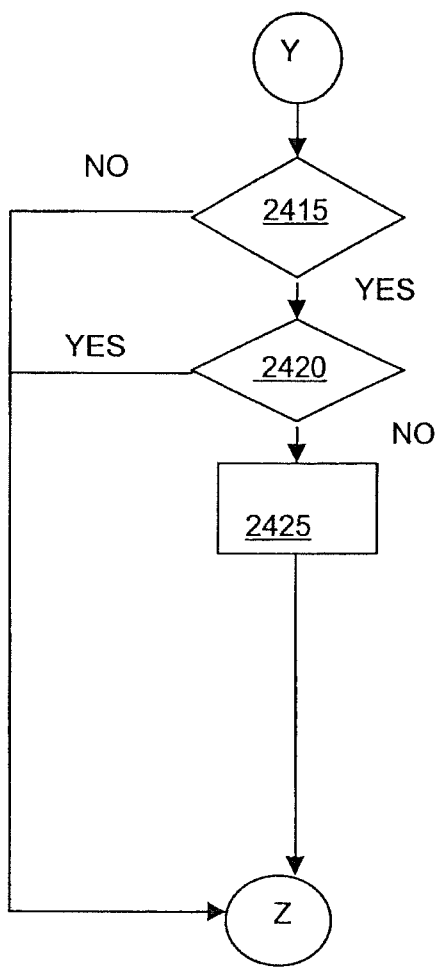
FIG. 24B depicts an algorithm for screening for diabetic nephropathy using routine urinalysis.

FIG. 24B depicts an illustrative algorithm for screening for diabetic nephropathy using routine urinalysis. If the member has a personal history of diabetes 2415 and has not had a urinalysis in the past year 2420, then HEALTHSCREEN will output a recommendation similar to the following recommendation 2425: "Because of your diabetes, a urinalysis is recommended within the next year to identify protein loss into the urine or a spot urine ratio (protein/creatinine) test is necessary to monitor and quantify known protein loss. More information on this Preventative Medicine topic may be found at http://www.edoc4u/diabetes.html." Members not meeting the network-determined criteria receive no recommendations from this algorithm, and the HEALTHSCREEN processing continues.

Figure 24C:
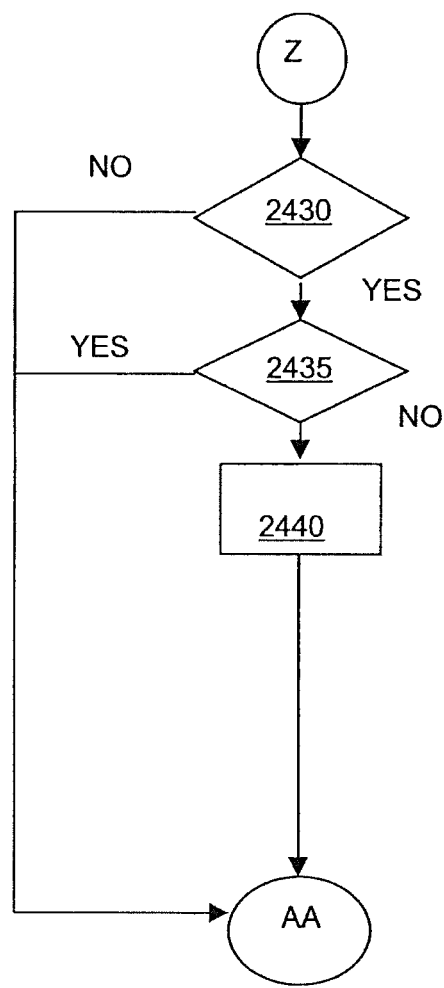
FIG. 24C depicts an algorithm for screening for diabetic serum glucose control using routine hemoglobin A1C blood level tests.

FIG. 24C depicts an illustrative algorithm for screening for diabetic serum glucose control using a routine hemoglobin A1C blood test. If the member has a personal history of diabetes 2430 and has not had a hemoglobin A1C blood test in the past three to six months 2435, then HEALTHSCREEN will output a recommendation similar to the following recommendation 2440: "Because of your diabetes, a blood hemoglobin A1C test is recommended within the next month to monitor your level of diabetic blood sugar control. Blood sugar control has been proven to slow down the progression of diabetic heart, kidney, and eye disease. Your hemoglobin A1C blood level may need to be checked as frequently as every three months until diabetic blood sugar control can be confirmed. More information on this Preventative Medicine topic may be found at http://www.edoc4u/diabetes.html." Members not meeting the network-determined criteria receive no recommendations from this algorithm, and the HEALTHSCREEN processing continues.

Figure 24D:
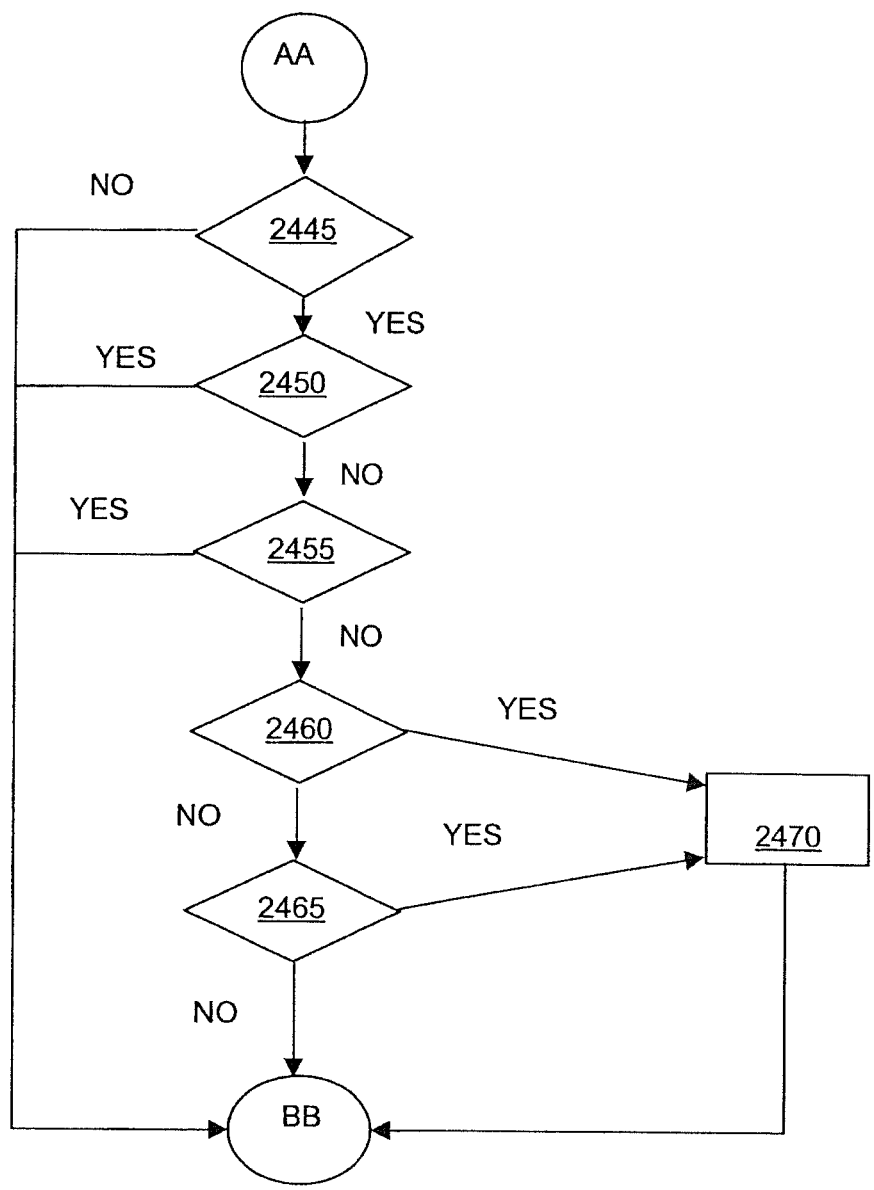
FIG. 24D depicts an algorithm for interventions that slow the progression of diabetic kidney disease by using angiotensin converting enzyme (ACE) inhibitors.

FIG. 24D depicts an illustrative algorithm for interventions that slow the progression of diabetic kidney disease by using angiotensin converting enzyme (ACE) inhibitors. If the member has a personal history of diabetes 2445, is not allergic to ACE inhibitors 2450 such as fosinopril (MONOPRIL), benazepril (LOTENSIN), lisinopril (PRINIVIL or ZESTRIL), ramipril (ALTACE), moexipril (UNIVASC), quinapril (ACCUPRIL), enalapril (VASOTEC), captopril (CAPOTEN), or trandolapril (MAVIK), is not currently taking an ACE inhibitor 2455, and has a personal history of hypertension 2460 or is known to be losing protein into the urine 2465, then HEALTHSCREEN will output a recommendation similar to the following recommendation 2470: "Use of ACE inhibitors by diabetics with hypertension or losing protein into the urine has been proven to extend kidney health and function by slowing down the progression of diabetic kidney disease. Starting an ACE inhibitor medication is recommended. More information on this Preventative Medicine topic may be found at http://www.edoc4u/diabetes.html." Members not meeting the network-determined criteria receive no recommendations from this algorithm, and the HEALTHSCREEN processing continues.

Figure 25A:
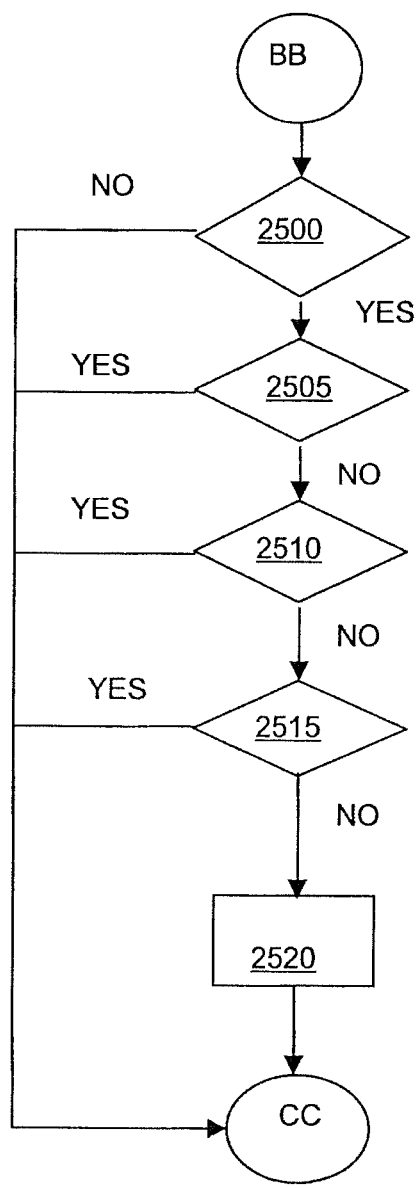
FIG. 25A depicts an algorithm for prevention of birth defects by taking folate each day.

FIG. 25A depicts an illustrative algorithm for prevention of birth defects by taking folate each day. If the member is female 2500, not postmenopausal 2505, has not had a hysterectomy 2510, and is not taking the recommended daily allowance (RDA) of folate each day 2515, then HEALTHSCREEN will output a recommendation similar to the following recommendation 2520: "Folate (or folic acid) at a dose of 1 mg each day is recommended to all women of childbearing age as it has been proven to prevent neural tube birth defects. More information on this Preventative Medicine topic may be found at http://www.edoc4u/vitamins.html."

Figure 25B:
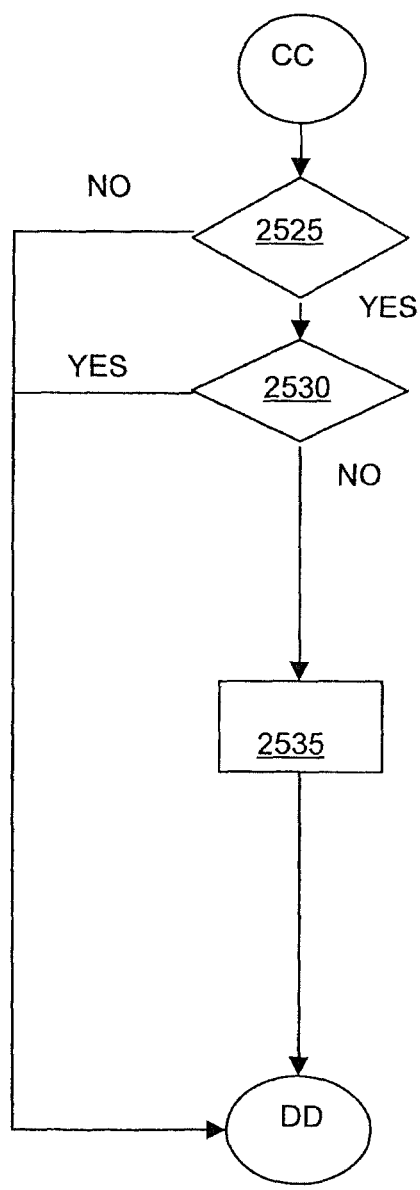
FIG. 25B depicts an algorithm for prevention of cardiac events by taking folate each day.

FIG. 25B depicts an illustrative algorithm for prevention of cardiac events by taking folate each day. If the member has a personal history of coronary artery disease (CAD) 2525 and is not taking the recommended daily allowance (RDA) of folate each day 2530, then HEALTHSCREEN will output a recommendation similar to the following recommendation 2535: "Folate (or folic acid) at a dose of 1 mg each day is recommended to all people with coronary artery disease to reduce their risk of recurrent cardiac events. More information on this Preventative Medicine topic may be found at http://www.edoc4u/vitamins.html." Members not meeting the network-determined criteria receive no recommendations from this algorithm, and the HEALTHSCREEN processing continues.

Figure 25C:
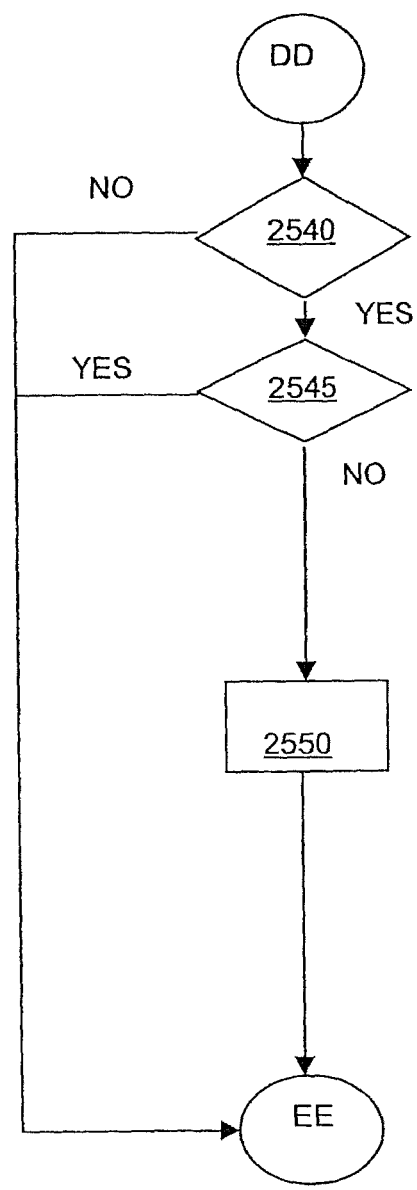
FIG. 25C depicts an algorithm for prevention of cardiac events by taking Vitamin E each day.

FIG. 25C depicts an illustrative algorithm for prevention of cardiac events by taking Vitamin E each day. If the member has a personal history of coronary artery disease (CAD) 2540 and is not taking the recommended daily allowance (RDA) of vitamin E each day 2545, then HEALTHSCREEN will output a recommendation similar to the following recommendation 2550: "Vitamin E at a dose of 400 IU (International units)

each day is recommended to all people with coronary artery disease to reduce their risk of recurrent cardiac events. More information on this Preventative Medicine topic may be found at http://www.edoc4u/vitamins.html." Members not meeting the network-determined criteria receive no recommendations from this algorithm, and the HEALTHSCREEN processing continues.

Figure 25D:
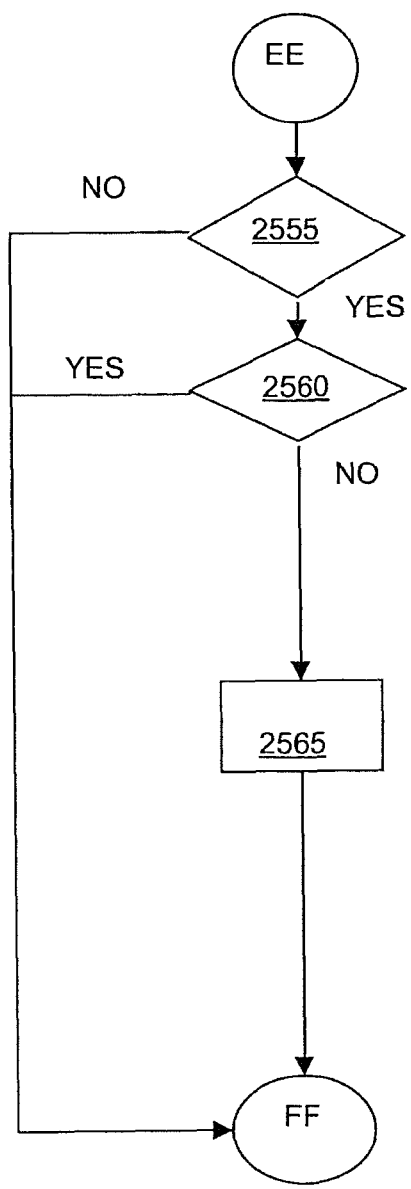
FIG. 25D depicts an algorithm for prevention of osteoporosis by taking calcium each day.

FIG. 25D depicts an illustrative algorithm for prevention of osteoporosis by taking calcium each day. If the member is female 2555 and is not taking the recommended daily allowance (RDA) of calcium each day 2560, then HEALTHSCREEN will output a recommendation similar to the following recommendation 2565: "Daily calcium of at least 1000 mg each day is recommended to all women to build strong bones and prevent osteoporosis, and preliminarily may help with pre-menstrual syndrome (PMS). More information on this Preventative Medicine topic may be found at http://www.edoc4u/vitamins.html." Members not meeting the network-determined criteria receive no recommendations from this algorithm, and the HEALTHSCREEN processing continues.

Figure 25E:
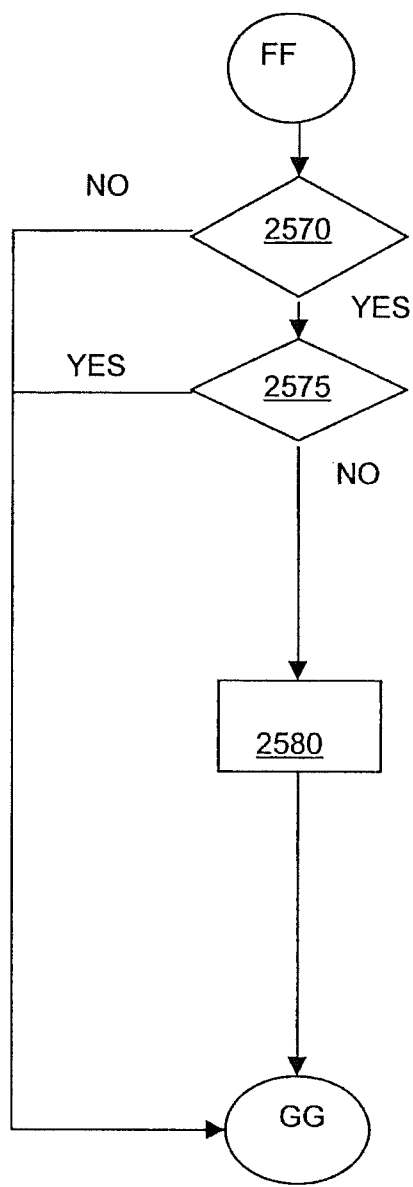
FIG. 25E depicts an algorithm for prevention of osteoporosis by taking Vitamin D each day.

FIG. 25E depicts an illustrative algorithm for prevention of osteoporosis by taking Vitamin D each day. If the member is female 2570 and is not taking the recommended daily allowance (RDA) of vitamin D each day 2575, then HEALTHSCREEN will output a recommendation similar to the following recommendation 2580: "Vitamin D at a dose of 400 IU (International Units) each day is recommended to all women to build strong bones and prevent osteoporosis. More information on this Preventative Medicine topic may be found at http://www.edoc4u/vitamins.html." Members not meeting the network-determined criteria receive no recommendations from this algorithm, and now the HEALTHSCREEN processing is complete.

Each component of each HEALTHSCREEN algorithm is continually evaluated by network administrative staff and may be modified in light of newly-identified disease risk factors. This evaluation process ensures that the HEALTHSCREEN will continue to generate the most current and accurate preventative medical recommendations. The list of preventative medical recommendations generated by these algorithms is provided directly to the member at least twice a year, as the HEALTHSCREEN. The HEALTHSCREEN can be provided by any manner of communication, i.e., mail, facsimile, telephone, or electronic mail. The member also has 24-hour access to his or her HEALTHSCREEN via the network.

The IPMS network also provides a STANDARD OF CARE (SOC) review for each member twice a year. The objective of the SOC review is to identify specific interventions that will limit both the severity and the future complications of an existing medical condition. The SOC recommendations are made by one or more network-selected, affiliated subspecialty physicians who each review the member's MEDCHART. For each medical condition disclosed on the member's MEDCHART, the IPMS network designates an appropriate subspecialty physician reviewer who is recognized as an expert on that specific medical condition. Each subspecialty physician selected by the IPMS network to make a STANDARD OF CARE recommendation on a given member's medical condition is provided with the member's MEDCHART for review.

For example, the network determines from a member's MEDCHART that the member has the diagnosis of diabetes. The member's MEDCHART is sent to a network-designated diabetes specialist for completion of the SOC review. This network-designated diabetes specialist may review the member's MEDCHART and learn that the member has not had acceptable serum glucose control over the past year. Based on this lack of recent diabetic control, the diabetes specialist offers the following STANDARD OF CARE recommendation: "Because of your diabetes, it is the recognized standard of medical care to check your blood Hemoglobin A1C values to monitor your diabetes at least every 3 months. Keeping blood Hemoglobin A1C values under 8.0 has been shown to slow progression of both diabetic kidney and diabetic eye disease. Your blood Hemoglobin A1C level should be drawn within the next month."

As another example, a network-designated subspecialty physician may evaluate a member's MEDCHART for laboratory tests or radiological studies necessitated by the member's current medications. A member who is taking lovastatin and has not had any blood work drawn in the last year might receive the following as a component of the STANDARD OF CARE review: "Because you currently take a medication called lovastatin, it is the recognized standard of medical care to check your serum liver function tests within the next year." Again, the subspecialty physician's SOC recommendations are provided to the network, incorporated with other SOC recommendations, and provided to the member as part of a complete STANDARD OF CARE review.

Once SOC recommendations are formulated by the network physician reviewers, the network physician reviewers input their recommendations to a web-based form for delivery to the network. The network compiles all reviewer inputs into one document, thus creating the member's SOC review. The SOC review encompasses all medical conditions listed in the member's MEDCHART. SOC recommendations can include physical examinations, labwork, X-rays, genetic or chromosomal screens, or other medical tests or procedures recommended to the member. The SOC review focuses on the member's existing medical conditions, in contrast to the HEALTHSCREEN, which targets prevention of future diseases through risk factor identification and reduction.

The SOC review is then provided to the member by the network. If the individual member has consented to having his or her personal non-network physician notified, then the SOC review is also provided to the member's personal physician via the DOCCONNECTOR service. Some of the diseases and medical conditions for which the medical services network will provide STANDARD OF CARE review are diabetes, high blood pressure, coronary artery disease, thyroid disease, inflammatory bowel disease, high cholesterol, peptic ulcer disease, valvular disease, cardiac dysrrhythmias, infections, esophageal reflux, iron deficiency, lung disease, and any other diseases at the discretion of the network subspecialty physicians.

If a designated subspecialty physician deems it to be in the best interest of the member, the physician may contact the member directly to gain additional medical information to assist in formulating member-specific SOC recommendations. The network engages as many subspecialty physicians as required for the completion of the member's STANDARD OF CARE review. The member is provided with this complete STANDARD OF CARE review by any manner of communication, such as telephone, postal mail, facsimile transmission, or electronic mail, and also has access through the network to this record. Communication between the network and the subspecialty physicians, and between the subspecialty physicians and the member can also occur by any manner of communication, such as facsimile transmission, voicemail, or electronic mail.

The communication necessary for implementation of the HEALTHSCREEN and the STANDARD OF CARE recommendation services is maintained by the network's DOCCONNECTOR service, which provides direct communication between network databases, members, Screening Procedure Centers (SPC), and, at each member's discretion, the member's personal physician. SPC's are medical facilities that agree to participate with the network to provide specified tests, physical examinations, and any of the other various recommended procedures for network members. An SPC becomes affiliated with the network by agreeing to provide timely feedback to the network once the recommended tests and procedures have been completed, as well as providing the actual results to the network. The DOCCONNECTOR service can forward these results to the member's personal physician for further interpretation. The SPC's agree to stay in close communication with the DOCCONNECTOR service administrators regarding the scheduling of these recommended tests and procedures such that if a specified time elapses (i.e. 30 days) and the test or procedure has not been performed, then the network administrators will be notified.

Typical SPCs include radiology centers, physician's offices, pharmacies, laboratories, DNA testing facilities, endoscopy centers, cardiac facilities, hearing centers, and vision centers. A radiology center may perform mammograms, X-rays, MRI's, CAT scans, EBCT scans, Ultrasounds, Nuclear Medicine tests such as Thallium, Sestamibi Scans, Bone Scans, Dual Energy X-Ray Absorptiometry (DEXA) scans, and interventional radiology or other radiological procedures. A physician's office may perform testicular exams, prostate exams, breast exams, pelvic exams, Pap Smears, blood pressure checks, or other organ-system examination or vital sign surveillance. A pharmacy/supply facility may perform prescription redemptions for medications and supplies such as Peak Flow meters, fingerstick glucometers, glucometer paperstrips, lancets, alcohol pads, and nasal strips for breathing. A laboratory facility may perform all routine and send-out blood tests such as complete blood counts (CBC), chemistries, lipid panels, liver function tests (LFT's), Hgb A1C, PSA, TSH; urine tests, sputum tests; semen tests; Pap smear analysis; stool tests; pathology examinations; serologies; titers; all cultures; and all hormonal level test. A DNA testing facility may perform western blot, southern blot, and northern blot analysis, chromosomal analysis, gene mapping, genetic screening, RNA testing, DNA testing, and any other gene related procedures. An endoscopy center may perform fiber optic endoscopy such as colonoscopy, flexible sigmoidoscopy, anoscopy, sinus endoscopy, vascular endoscopy, and esophagogastroduodenoscopy, or other procedures. A cardiac facility may perform EKG's, exercise and non-exercise treadmill tests, stress echoes, Pet scans, cardiac viability tests, cardiac catheterization and angioplasty, as well as other cardiac procedures. Hearing centers may perform routine hearing evaluations, ABR's, hearing aid tests, and any other hearing-related tests. A vision center may perform routine refraction, optometry exams, intraocular pressure measurement, diabetic and hypertensive retinopathy detection and surveillance exams, visual acuity check, and cataract exams, as well as any other eye/vision related test.

The DOCCONNECTOR service operating system resides on its own server. The DOCCONNECTOR service may be web-based, a wide area network, or both, and includes at least one e-mail system. The DOCCONNECTOR service provides each member with his or her test results, which may be accompanied by an interpretation by the member's personal physician. Results and interpretations are temporarily stored on the DOCCONNECTOR server in complete form. After an appropriate period such as 180 days, the DOCCONNECTOR server provides this medical data to the network for permanent storage and incorporation into the member's MEDCHART. The DOCCONNECTOR service can utilize MICROSOFT ACCESS 97 or other suitable software known in the art to monitor and record time-sensitive events such as non-network physician responses to network communications, member scheduling with each SPC, and each member's completion of network recommendations, as well as automatically sending related reminders, warnings, and other notifications as appropriate. The preferred means of communication for the DOCCONNECTOR service is electronic mail, but other means of communication can be used, such as postal mail, facsimile transmission, or the telephone.

Each member may choose to have his or her HEALTHSCREEN and STANDARD OF CARE review sent to his or her personal non-network physician for review. If the member chooses this option, then the DOCCONNECTOR service activates, and then the HEALTHSCREEN and STANDARD OF CARE recommendations are provided to the member's personal physician by any manner of communication, such as telephone, postal mail, facsimile transmission, or electronic mail. The member's personal physician has the option of agreeing or disagreeing with each HEALTHSCREEN or SOC recommendation. If the member's personal physician disagrees with a network recommendation or does not respond within a predefined period of time, such as 30 days, then the network notifies the DOCCONNECTOR administrators and the member of his or her personal physician's disagreement or failure to respond. On all e-mail communications from the medical network, the member's physician is provided with a "communication box" to have forwarded to the member by the DOCCONNECTOR service. The "communication box" is a pop-up window in an email message used to relay physician comments from the member's personal physician on the stated recommendation and its implementation to the member. All the above communications and each of the following communication options are tracked and permanently stored by time, date, subject, and parties involved by the DOCCONNECTOR service.

If the member's personal physician agrees with a recommendation, then the member's personal physician has three options regarding each medical recommendation. In the first option, the member's personal physician agrees with the network recommendation and communicates back to the medical network that he or she will personally perform the recommended procedure or test. The member's physician may use the "communication box" to provide the patient with the necessary information to complete this recommendation, such as scheduling an upcoming office appointment time and date. Other information that could be included in the "communication box" would be office laboratory blood draw procedures and times, medical procedure and lab costs, insurance coverage of these costs, and any other information that the member's personal physician wants to include in the communication. The medical network then notifies the member via the DOCCONNECTOR service that the physician desires to complete the network recommendation personally and will also forward to the member the "communication box" contents, if applicable. The DOCCONNECTOR service will request that the member update the member's network MEDCHART when this procedure has been completed. The DOCCONNECTOR service will periodically prompt the member about the status of these recommendations to encourage completion of the recommended medical procedures or tests and subsequent updating of the member's MEDCHART record.

In the second option, the member's personal physician agrees with the network recommendation and communicates back to the medical network that he or she wants a participating Screening Procedure Center (SPC) to perform the recommended procedure or test either by the personal physician's direct orders, or in some cases, by the order of medical network physicians. When this request is made by the member's personal physician or by a network physician, the network will request through the DOCCONNECTOR service that an appropriate SPC complete the medical procedure or test. The network SPC will contact the member to schedule and perform the recommended medical procedure or tests. The SPC will then provide the medical procedure or test results back to the network. The network provides the results to the member's personal physician, who originally ordered the procedure or test. The member's personal physician may then add an interpretation of the obtained results in the "communication box" and forward both back to the network. The network will, through the DOCCONNECTOR service, provide the results and personal physician interpretation to the member. If network physicians ordered the medical procedure or test, the network physicians will interpret the results, then providing both the results and the interpretation to the member. In this situation, the results and interpretation may also be provided to the member's personal physician, with member approval. Additionally, if the member's personal physician does not provide a signed interpretation in the "communication box" of the medical procedure or test results to the network in a predefined period of time, then the network will notify the member of their personal physician's response or failure to respond. Finally, whether the member's personal physician or a network physician interprets the results, the results and interpretation will again be temporarily stored on the DOCCONNECTOR server for approximately 180 days, then uploaded to the network to become part of the member's permanent MEDCHART.

In the third option, the member's personal physician agrees with the network recommendation and communicates back to the medical network that he or she wants a non-network Screening Procedure Center (SPC) to perform the recommended procedure or test. The Screening Procedure Center may be a facility the personal physician routinely uses. The member's personal physician is again given the option to use the contents of the "communication box" to provide the member with the necessary information to complete this recommendation with a non-network SPC. The network then notifies the member via the DOCCONNECTOR service that his or her physician wishes to complete this recommendation through a non-network SPC, and will also forward to the member the "communication box" from the member's personal physician. Finally, the network will request that the member update the member's MEDCHART when this procedure has been performed. The network's DOCCONNECTOR service will periodically prompt the member about the status of these recommendations to encourage completion of the medical procedures or tests and subsequent updating of the member's MEDCHART record.

In addition to the DOCCONNECTOR service, the network provides a parallel DIRECTDOC communication service that allows members to correspond directly with licensed, board-certified physicians at the network in reference to any health-related question a member might have about health optimization, preventative medicine, standards of medical care, specific disease entities, or individual health concerns. The DIRECTDOC service operates on a dedicated server that allows for member-to-network communication, and this service remains distinct from the DOCCONNECTOR service. In a preferred embodiment, each member is granted five free e-mails each year, with each e-mail limited to 250 words. The number of free e-mails and their maximum length may vary as deemed appropriate by network administrators. E-mail response should be provided in two business days. E-mail messages exceeding the limits would result in a member charge per hour of physician time allotted to respond to the email. A member who has used up the allotted free e-mails or has sent an e-mail of more than the maximum length is notified that completion of the DIRECTDOC response will incur charges. If the member still desires a response at the quoted rate per hour of physician time, then the DIRECTDOC communicates a response and the network bills the member accordingly.

The network also allows emergency medical record retrieval for network members. The network EMERGENCY MEDCHART service provides the member with an option to allow emergency access to a pre-authorized subset of the member's MEDCHART information, so that an emergency health care provider can access pre-authorized member medical information if an emergency situation occurs and a member is unable to give a medical history or even grant consent for medical record retrieval. This subset, called the EMERGENCY MEDCHART, is a separate record activated or inactivated solely at the member's discretion and may contain all the member's MEDCHART information. When the EMERGENCY MEDCHART service is activated, the member is allowed to methodically evaluate all of the data in his or her MEDCHART, making personal determinations as to whether to include each MEDCHART data field in the EMERGENCY MEDCHART. If a member does not preauthorize any medical data from a specific field of their MEDCHART, then the corresponding data field in the EMERGENCY MEDCHART will be empty. The EMERGENCY MEDCHART is permanently and securely stored on the network separate from the MEDCHART. Only data preauthorized by the member is accessible to a health care provider under emergency circumstances. The EMERGENCY MEDCHART is modifiable by the member only. Modification could occur through any manner of communication, such as telephone, postal mail, facsimile transmission, or electronic mail. The EMERGENCY MEDCHART is provided on the network and is accessible with appropriate authorization on a 24-hour basis. This EMERGENCY MEDCHART can be accessed and then transferred by any manner of communication, such as postal mail, facsimile transmission, or electronic mail.

Critical information from the EMERGENCY MEDCHART service is provided by the network to members on portable WALLETCARDs. Each WALLETCARD may contain the following fields from the member's EMERGENCY MEDCHART: allergies, medications, past medical history, and procedures by which emergency health care personnel may access EMERGENCY MEDCHART information. WALLETCARDs are only generated if the member has chosen to activate the network EMERGENCY MEDCHART service. WALLETCARDs can be provided to the members by any manner of communication, such as postal mail, facsimile transmission, or electronic mail, and may be printed, magnetically or optically encoded on permanent media, transmitted in a form suitable for storage and display on a personal data assistant, or provided in any other suitable format. A network computer program analyzes the member's EMERGENCY MEDCHART twice a year to update information for the WALLETCARD, then forwards the updated WALLETCARD to the member. The WALLETCARD information also includes a network password for emergency health care providers to use to gain access to the member's EMERGENCY MEDCHART. The WALLETCARDs may also include space for the member to input personal emergency contact names, phone numbers, and other information. By use of the member-specific network passwords encoded on WALLET-CARDs, emergency health care providers can register with the network and access the EMERGENCY MEDCHART for that specific member. Prior to EMERGENCY MEDCHART access, the requesting emergency health care provider must provide their name, position, and current business address, as well as identifying their current location and present role in the management of the medical care of this member. The requesting emergency health care provider is also required to read and agree with a statement of confidentiality for the release of these medical records. The network stores a data record of all persons who access the EMERGENCY MEDCHART service and informs the member when his or her record is accessed. This notification to the member can be through any manner of communication, i.e. postal mail, facsimile transmission, or electronic mail from the network.

The principles, embodiments, and modes of operation of the present invention have been set forth in the foregoing specification. The embodiments disclosed herein should be interpreted as illustrating the present invention and not as restricting it. The foregoing disclosure is not intended to limit the range of equivalent structure available to a person of ordinary skill in the art in any way, but rather to expand the range of equivalent structures in ways not previously contemplated. Numerous variations and changes can be made to the foregoing illustrative embodiments without departing from the scope and spirit of the present invention.

I claim:

1. A system, comprising:
    a memory to store records associated with a plurality of users; and
    one or more computer devices to:
        receive data from a user,
        store the data in a record in the memory,
            where the record is associated with the user,
        automatically and periodically evaluate the data, in the record, to generate a set of first recommendations,
            where each first recommendation, in the set of first recommendations, relates to a recommended action to be taken by the user to mitigate a risk, of the user, for developing a new condition,
        automatically and periodically analyze data in the record to identify a plurality of existing conditions of the user,
        select a plurality of individuals based on the plurality of existing conditions,
            each of the plurality of individuals being designated as an expert for one of the plurality of existing conditions,
        transmit the data, from the record, to each of the plurality of individuals,
        receive a respective second recommendation from each of at least two of the plurality of individuals,
            where each of the respective second recommendations relates to another recommended action to be taken by the user to limit a severity or a future complication relating to one of the plurality of existing conditions,
        compile the respective second recommendations, from the at least two of the plurality of individuals, to generate a document that includes a set of second recommendations of the respective second recommendations,
            where the set of second recommendations is different from the set of first recommendations, and
        provide, to the user, the set of first recommendations and the document including the set of second recommendations.

2. The system of claim 1, where the one or more computer devices are to repeatedly perform the automatic and periodic evaluating of the data at a first plurality of scheduled times, and the one or more computer devices are to repeatedly perform the automatic and periodic analyzing of the data in the record, the selecting of the plurality of individuals, and the transmitting of the data to each of the plurality of individuals at a second plurality of scheduled times, where the first plurality of scheduled times is independent from the second plurality of scheduled times.

3. A method performed by one or more computer devices, the method comprising:
    receiving, by at least one of the one or more computer devices, medical data associated with a user;
    storing, by at least one of the one or more computer devices, the medical data in a medical record associated with the user;
    automatically and periodically performing, by at least one of the one or more computer devices, an evaluation of the medical data, in the medical record, to generate a set of first recommendations,
        where each first recommendation, in the set of first recommendations, relates to a recommended action to be taken by the user to prevent a future medical condition of the user;
    automatically and periodically analyzing, by at least one of the one or more computer devices, the data in the medical record to identify a plurality of existing medical conditions of the user;
    selecting, by at least one of the one or more computer devices and based on the plurality of existing medical conditions, a plurality of physicians specializing in the plurality of existing medical conditions;
    transmitting, by at least one of the one or more computer devices, the medical data, from the medical record, to each of the plurality of physicians;
    receiving, by at least one of the one or more computer devices and from each of at least two of the plurality of physicians, a respective second recommendation regarding treatment of one of the plurality of existing medical conditions;
    compiling, by at least one of the one or more computer devices, the respective second recommendations, from the at least two of the plurality of physicians, to generate a document that includes a set of second recommendations of the respective second recommendations,
        where the set of second recommendations is different from the set of first recommendations; and
    providing, by at least one of the one or more computer devices and to the user, the set of first recommendations and the document including the set of second recommendations.

4. The method of claim 3, where automatically and periodically performing the evaluation of the medical data is repeatedly performed at a first plurality of scheduled times,
    where automatically and periodically analyzing the data in the record, selecting the plurality of physicians, and transmitting the medical data to each of the plurality of physicians are repeatedly performed at a second plurality of scheduled times, and
    where the first plurality of scheduled times is independent from the second plurality of scheduled times.

5. The method of claim 3, where the medical record includes a plurality of fields, and where storing the medical data in the medical record includes:
  automatically populating at least one of the plurality of fields of the medical record with the medical data associated with the user.
6. The method of claim 3, further comprising:
  receiving, from the user, information regarding a set of users permitted to access the medical record; and
  selectively permitting access to the medical record based on the information regarding the set of users.
7. The method of claim 3, where selecting the plurality of physicians includes:
  analyzing the medical data, in the medical record, to identify a particular disease of the user; and
  selecting one of the plurality of physicians who specializes in the particular disease.
8. The method of claim 3, where automatically and periodically performing the evaluation of the medical data and selecting the plurality of physicians are performed based only on the medical data in the medical record.
9. The method of claim 3, further comprising:
  receiving, from the user, information identifying a particular physician to receive the set of first recommendations and the set of second recommendations; and
  providing, based on the received information, the set of first recommendations and the set of second recommendations to the particular physician.
10. The method of claim 3, further comprising:
  receiving, from the user, selection of a subset of the medical data in the medical record;
  creating a separate medical record, associated with the user, using the subset of the medical data, where the separate medical record is distinct from the medical record; and
  providing, to a particular physician, access to the separate medical record.
11. The method of claim 3, where providing the set of first recommendations and the document including the set of second recommendations includes:
  encrypting data associated with the set of first recommendations and the set of second recommendations, and
  transmitting the encrypted data to the user.
12. The method of claim 3, further comprising:
  providing, to the user, access to the medical data in the medical record associated with the user;
  receiving modification of the medical data to form modified medical data; and
  storing the modified medical data in the medical record.
13. The method of claim 3, further comprising:
  receiving, from the user, permissions associated with modifying or viewing the medical data in the medical record; and
  restricting subsequent modifying or viewing of the medical data based on the received permissions.
14. The system of claim 1, where the record includes a plurality of fields, and
  where, when storing the data in the record, the one or more computer devices are to automatically populate at least one of the plurality of fields of the record with the data received from the user.
15. The system of claim 1, where the one or more computer devices are further to:
  receive, from the user, information regarding a set of users permitted to access the record, and
  selectively permit subsequent access to the record based on the information regarding the set of users.

16. The system of claim 1, where the one or more computer devices are to automatically evaluate the data and select the plurality of individuals based only on the data in the record.
17. The system of claim 1, where the one or more computer devices are further to:
  receive, from the user, selection of a subset of the data in the record,
  create a separate record, associated with the user, using the subset of the data, where the separate record is distinct from the record, and
  provide, to a particular individual that is separate from the user, access to the separate record.
18. A memory device comprising:
  a plurality of instructions which, when executed by one or more processors of one or more computer devices, cause the one or more processors to:
    receive medical data associated with a user;
    automatically populate a medical record, associated with the user, using the medical data received from the user;
    automatically perform, at a first plurality of scheduled times, an evaluation of the medical data, in the medical record, to generate a set of first recommendations,
      where each first recommendation, in the set of first recommendations, relates to a recommended action to be taken by the user to mitigate a risk, of the user, for developing a new medical condition;
    automatically perform, at a second plurality of scheduled times, an analysis of the medical data, in the medical record, to identify a plurality of existing medical conditions of the user,
      where the second plurality of scheduled times is independent of the first plurality of scheduled times;
    select, based on the plurality of existing medical conditions, a plurality of physicians specializing in the plurality of existing medical conditions;
    transmit the medical data, from the medical record, to each of the plurality of physicians;
    receive, from each of the plurality of physicians, a respective second recommendation regarding treatment of one of the plurality of existing medical conditions of the user;
    compile the respective second recommendations, from the plurality of physicians, to generate a document that includes a set of second recommendations of the respective second recommendations,
      where the set of second recommendations is different from the set of first recommendations; and
    provide, to the user, the set of first recommendations and the document including the set of second recommendations.
19. The memory device of claim 18, where one or more instructions, of the plurality of instructions, to select the plurality of physicians include:
  one or more instructions which, when executed by the one or more processors, cause the one or more processors to:
    analyze the medical data, in the medical record, to identify a particular disease of the user; and
    select one of the plurality of physicians who specializes in the particular disease.
20. The memory device of claim 18, where the plurality of instructions further cause the one or more processors to:
  receive, from the user, information identifying a particular physician to receive the set of first recommendations and the set of second recommendations; and provide, based on the received information, the set of first recommendations and the set of second recommendations to the particular physician.

21. The memory device of claim 18, where the plurality of instructions further cause the one or more processors to:
receive, from the user, selection of a subset of the medical data in the medical record;
create a separate medical record, associated with the user, using the subset of the medical data, where the separate medical record is distinct from the medical record; and
provide, to a particular physician, access to the separate medical record.

22. The memory device of claim 18, where one or more instructions, of the plurality of instructions, to provide the set of first recommendations and the document including the set of second recommendations include:
one or more instructions which, when executed by the one or more processors, cause the one or more processors to:
encrypt data associated with the set of first recommendations or the set of second recommendations, and
transmit the encrypted data to the user.

23. The memory device of claim 18, where the plurality of instructions further cause the one or more processors to:
provide, to the user, access to the medical data in the medical record associated with the user;
receive modification of the medical data to form modified medical data; and
store the modified medical data in the medical record.

24. The memory device of claim 18, where the plurality of instructions further cause the one or more processors to:
receive, from the user, a permission associated with modifying or viewing the medical data in the medical record; and
restrict, based on the received permission, a subsequent request for modifying or viewing the medical data.

* * * * *